US009597382B2

(12) United States Patent
Tsunoda et al.

(10) Patent No.: US 9,597,382 B2
(45) Date of Patent: Mar. 21, 2017

(54) KNTC2 PEPTIDES AND VACCINES CONTAINING THE SAME

(71) Applicant: ONCOTHERAPY SCIENCE, INC., Kanagawa (JP)

(72) Inventors: Takuya Tsunoda, Kanagawa (JP); Ryuji Osawa, Kanagawa (JP); Sachiko Yoshimura, Kanagawa (JP); Tomohisa Watanabe, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 14/772,003

(22) PCT Filed: Mar. 11, 2014

(86) PCT No.: PCT/JP2014/001350
§ 371 (c)(1),
(2) Date: Sep. 1, 2015

(87) PCT Pub. No.: WO2014/141683
PCT Pub. Date: Sep. 18, 2014

(65) Prior Publication Data
US 2016/0008445 A1    Jan. 14, 2016

Related U.S. Application Data

(60) Provisional application No. 61/777,334, filed on Mar. 12, 2013.

(51) Int. Cl.
| | |
|---|---|
| *C07K 14/00* | (2006.01) |
| *A61K 39/00* | (2006.01) |
| *C07K 14/47* | (2006.01) |
| *G01N 33/50* | (2006.01) |
| *C07K 7/06* | (2006.01) |
| *C07K 16/18* | (2006.01) |
| *G01N 33/574* | (2006.01) |
| *A61K 38/00* | (2006.01) |

(52) U.S. Cl.
CPC ........... *A61K 39/0011* (2013.01); *C07K 7/06* (2013.01); *C07K 14/47* (2013.01); *C07K 16/18* (2013.01); *G01N 33/505* (2013.01); *G01N 33/57484* (2013.01); *A61K 38/00* (2013.01); *A61K 2039/5154* (2013.01)

(58) Field of Classification Search
None
See application file for complete search history.

(56) References Cited

U.S. PATENT DOCUMENTS

| 6,703,491 | B1 * | 3/2004 | Homburger | A01K 67/0333 435/252.3 |
| 7,189,546 | B2 * | 3/2007 | Fukushima | C07K 14/47 424/94.1 |
| 7,507,536 | B2 * | 3/2009 | Van Criekinge | C12Q 1/6886 435/6.14 |
| 7,531,300 | B2 | 5/2009 | Nakamura et al. | |
| 7,943,295 | B2 | 5/2011 | Nakamura et al. | |
| 7,998,695 | B2 | 8/2011 | Nakamura et al. | |
| 8,044,193 | B2 | 10/2011 | Nakamura et al. | |
| 8,383,590 | B2 | 2/2013 | Tsunoda et al. | |
| 8,575,070 | B2 * | 11/2013 | Watt | C07K 1/047 506/24 |
| 8,623,829 | B2 | 1/2014 | Tsunoda et al. | |
| 8,685,641 | B2 | 4/2014 | Nakamura et al. | |
| 8,759,481 | B2 | 6/2014 | Tsunoda et al. | |
| 9,067,973 | B2 | 6/2015 | Tsunoda et al. | |
| 2003/0086934 | A1 | 5/2003 | Botstein et al. | |
| 2006/0024692 | A1 | 2/2006 | Nakamura et al. | |
| 2006/0093617 | A1 | 5/2006 | Buyse et al. | |
| 2009/0062512 | A1 | 3/2009 | Hildebrand et al. | |
| 2009/0317392 | A1 | 12/2009 | Nakamura et al. | |
| 2010/0040641 | A1 * | 2/2010 | Tsunoda | A61K 31/7088 424/185.1 |
| 2010/0281003 | A1 * | 11/2010 | Jochim | G06F 19/16 707/692 |
| 2011/0263012 | A1 | 10/2011 | Nakamura et al. | |
| 2012/0010090 | A1 | 1/2012 | Nakamura et al. | |
| 2012/0014996 | A1 | 1/2012 | Nakamura et al. | |
| 2012/0276588 | A1 * | 11/2012 | Hallen-Adams | C07K 14/375 435/69.1 |
| 2014/0248300 | A1 | 9/2014 | Tsunoda et al. | |

(Continued)

FOREIGN PATENT DOCUMENTS

| CN | 102863514 A | 1/2013 |
| EP | 1022286 A1 | 7/2000 |

(Continued)

OTHER PUBLICATIONS

Engelhard, Current Opinion in Immunology vol. 6 p. 13 (1994).*
Guo, et al Nature vol. 360 p. 384 (1992).*
Rammensee et al, Immunogenetics vol. 41 p. 178 (1995.*
Shastri et al J. Immunol. 1995 vol. 155 p. 4339.*
Adams, et al., "Prediction of binding to MHC class I molecules," *J Immunol Methods*, vol. 185(2), pp. 181-190 (1995).
Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (2002).
Boon, "Tumor Antigens Recognized by Cytolytic T Lymphocytes: Present Perspectives for Specific Immunotherapy," *Int J Cancer*, vol. 54(2), pp. 177-180 (1993).
Boon, et al., "Human Tumor Antigens Recognized by T Lymphocytes," *J Exp Med.*, vol. 183(3), pp. 725-729 (1996).
Butterfield, et al., "Generation of Human T-cell Responses to an HLA-A2.1-restricted Peptide Epitope Derived from α-Fetoprotein," *Cancer Res.*, vol. 59(13), pp. 3134-3142 (1999).

(Continued)

*Primary Examiner* — Sheela J Huff
(74) *Attorney, Agent, or Firm* — Kilpatrick Townsend & Stockton LLP

(57) ABSTRACT

Peptide vaccines against cancer are described herein. In particular, isolated epitope peptides derived from the KNTC2 gene that elicit CTLs and thus are suitable for use in the context of cancer immunotherapy are provided. The inventive peptides encompass both KNTC2-derived peptides and modified versions thereof, provided such modified versions retain the requisite CTL inducibility of the original sequences.

12 Claims, 3 Drawing Sheets

(56) References Cited

U.S. PATENT DOCUMENTS

| | | | |
|---|---|---|---|
| 2016/0046678 A1* | 2/2016 | Roschke | C07K 16/24 424/134.1 |
| 2016/0117441 A1* | 4/2016 | Bremel | G06F 19/18 706/21 |

FOREIGN PATENT DOCUMENTS

| | | |
|---|---|---|
| EP | 1757306 A1 | 2/2007 |
| WO | 98/45433 A1 | 10/1998 |
| WO | 02/078524 A2 | 10/2002 |
| WO | 2004/030615 A2 | 4/2004 |
| WO | 2004/031413 A2 | 4/2004 |
| WO | 2004/055050 A2 | 7/2004 |
| WO | 2004/058153 A2 | 7/2004 |
| WO | 2005/001138 A2 | 1/2005 |
| WO | 2005/016962 A2 | 2/2005 |
| WO | 2005/028676 A2 | 3/2005 |
| WO | 2005/097189 A1 | 10/2005 |
| WO | 2006/085684 A2 | 8/2006 |
| WO | 2007/013480 A2 | 2/2007 |
| WO | 2007/013665 A2 | 2/2007 |
| WO | 2007/064743 A2 | 6/2007 |
| WO | 2007/121147 A2 | 10/2007 |
| WO | 2007/150077 A2 | 12/2007 |
| WO | 2008/102557 A1 | 8/2008 |
| WO | 2009/025116 A1 | 2/2009 |
| WO | 2009/099580 * | 8/2009 |
| WO | 2011/039289 A1 | 4/2011 |

OTHER PUBLICATIONS

Ciferri, et al., "Architecture of the Human Ndc80-Hec1 Complex, a Critical Constituent of the Outer Kinetochore," *J Biol Chem.*, vol. 280(32), pp. 29088-29095 (2005).

Coulie, et al., "Cytolytic T-cell responses of cancer patients vaccinated with a MAGE antigen," *Immunol Rev.*, vol. 188, pp. 33-42 (2002).

Dionne, et al., "Functional characterization of CTL against gp100 altered peptide ligands," *Cancer Immunol. Immunother.*, vol. 52(4), pp. 199-206 (2003).

Dionne, et al., "Her-2/neu altered peptide ligand-induced CTL responses: implications for peptides with increased HLA affinity and T-cell-receptor interaction," *Cancer Immunol. Immunother.*, vol. 53(4), pp. 307-314 (2004).

Falk, et al., "Allele-specific motifs revealed by sequencing of self-peptide eluted from MHC molecules," *Nature*, vol. 351(6324), pp. 290-296 (1991).

Fujie, et al., "A Mage-1-Encoded HLA-A24-Binding Synthetic Peptide Induces Specific Anti-Tumor Cytotoxic T Lymphocytes," *Int J Cancer*, vol. 80(2), pp. 169-172 (1999).

Harada, et al., "Kinesin superfamily protein-derived peptides with the ability to induce glioma-reactive cytotoxic T lymphocytes in human leukocyte antigen-A24+glioma patients," *Oncol Rep.*, vol. 17(3), pp. 629-636 (2007).

Harris, et al., "Structure and Function of the p53 Tumor Suppressor Gene: Clues for Rational Cancer Therapeutic Strategies," *J Natl Cancer Inst.*, vol. 88(20), pp. 1442-1455 (1996).

Hawkins, et al., "Identification of Breast Cancer Peptide Epitopes Presented by HLA-A*0201," *J Proteome Res.*, vol. 7(4), pp. 1445-1457 (2008).

Hayama, et al., "Activation of CDCA1-KNTC2, Members of Centromere Protein Complex, Involved in Pulmonary Carcinogenesis," *Cancer Res.*, vol. 66(21), pp. 10339-10348 (2006).

Hoffmann, et al., "The Ability of Variant Peptides to Reverse the Nonresponsiveness to the Wild-Type Sequence $p53_{264-272}$ Epitope," *J Immunol*, vol. 168(3), pp. 1338-1347 (2002).

Kakiuchi, et al., "Genome-Wide Analysis of Organ-Preferential Metastasis of Human Small Cell Lung Cancer in Mice," *Mol Cancer Res.*, vol. 1(7), pp. 485-499 (2003).

Kakiuchi, et al., "Prediction of sensitivity of advanced non-small cell lung cancers to gefitinib (Iressa, ZD1839)," *Hum Mol Genet.*, vol. 13(24), pp. 3029-3043 (2004).

Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (1999).

Kikuchi, et al., "Expression profiles of non-small cell lung cancers on cDNA microarrays: Identification of genes for prediction of lymph-node metastasis and sensitivity to anti-cancer drugs," *Oncogene*, vol. 22(14), pp. 2192-2205 (2003).

Kondo, et al., "Prominent Roles of Secondary Anchor Residues in Peptide Binding to HLA-A24 Human Class I Molecules," *J Immunol.*, vol. 155(9), pp. 4307-4312 (1995).

Kubo, et al., "Definition of Specific Peptide Motifs for Four Major HLA-A Alleles," *J Immunol.*, vol. 152(8), pp. 3913-3924 (1994).

Oiso, et al., "A Newly Identified *Mage*-3-Derived Epitope Recognized by HLA-A24-Restricted Cytotoxic T Lymphocytes," *Int J Cancer*, vol. 81(3), pp. 387-394 (1999).

Parker, et al., "Scheme for Ranking Potential HLA-A2 Binding Peptides Based on Independent Binding of Individual Peptide Side-Chains," *J Immunol.*, vol. 152(1), pp. 163-175 (1994).

Rammensee, et al., "MHC ligands and peptide motifs: first listing," *Immunogenetics*, vol. 41(4), pp. 178-228 (1995).

Rosenberg, et al., "Cancer immunotherapy: moving beyond current vaccines," *Nat Med.*, vol. 10(9), pp. 909-915 (2004).

Schueler-Furman, "Structure-based prediction of binding peptides to MHC class I molecules: Application to a broad range of MHC alleles," *Protein Sci.*, vol. 9(9), pp. 1838-1846 (2000).

Suda, et al., "Identification of *secernin 1* as a novel immunotherapy target for gastric cancer using the expression profiles of cDNA microarray," *Cancer Sci.*, vol. 97(5), pp. 411-419 (2006).

Suzuki, et al., "Identification of COX17 as a Therapeutic Target for Non-Small Cell Lung Cancer," *Cancer Res.*, vol. 63(21), pp. 7038-7041 (2003).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (1997).

Van Der Burg, et al., "Immunogenicity of Peptides Bound to MHC Class I Molecules Depends on the MHC-Peptide Complex Stability," *J Immunol.*; vol. 156(9), pp. 3308-3314 (1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (1999).

Wigge, et al., "The Ndc8Op Complex from *Saccharomyces cerevisiae* Contains Conserved Centromere Components and Has a Function in Chromosome Segregation," *J Cell Biol.*, vol. 152(2), pp. 349-360 (2001).

Zaremba, et al., "Identification of an Enhancer Agonist Cytotoxic T Lymphocyte Peptide from Human Carcinoembryonic Antigen," *Cancer Res.*, vol. 57(20), pp. 4570-4577 (1997).

Zembutsu, et al., "Gene-expression profiles of human tumor xenografts in nude mice treated orally with the EGFR tyrosine kinase inhibitor ZD1839," *Int J Oncol.*, vol. 23(1), pp. 29-39 (2003).

U.S. Appl. No. 14/989,741, filed Jan. 6, 2016, 138 pages.

\* cited by examiner a b c a b c

SEQUENCE LISTING

<160> NUMBER OF SEQ ID NOS: 84

<210> SEQ ID NO 1
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 1

```
Gly Leu Asn Glu Glu Ile Ala Arg Val
1               5

<210> SEQ ID NO 2
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 2

Phe Leu Tyr Gly Phe Leu Cys Pro Ser
1               5

<210> SEQ ID NO 3
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 3

Ile Val Ala Ala Leu Val Trp Leu Ile
1               5

<210> SEQ ID NO 4
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 4

Ala Leu Asn Glu Gln Ile Ala Arg Leu
1               5

<210> SEQ ID NO 5
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 5

Gly Leu Ser Glu Ala Met Asn Glu Leu
1               5

<210> SEQ ID NO 6
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 6

Lys Leu Asn Gly Leu Asn Glu Glu Ile
1               5

<210> SEQ ID NO 7
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 7
```

```
Ala Leu Val Trp Leu Ile Asp Cys Ile
1               5

<210> SEQ ID NO 8
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 8

Met Val Ala Thr His Val Gly Ser Val
1               5

<210> SEQ ID NO 9
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 9

Leu Leu Asn Glu Thr Glu Glu Glu Ile
1               5

<210> SEQ ID NO 10
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 10

His Leu Glu Glu Gln Ile Ala Lys Val
1               5

<210> SEQ ID NO 11
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 11

Ile Leu Asp Gln Lys Leu Asn Gly Leu
1               5

<210> SEQ ID NO 12
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 12

Asn Leu Gln Arg Leu Leu Glu Met Val
1               5

<210> SEQ ID NO 13
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 13

Ile Ile Asp Asn Gln Lys Tyr Ser Val
```

```
<210> SEQ ID NO 14
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 14

Phe Ile Gln Gln Cys Ile Arg Gln Leu
1               5

<210> SEQ ID NO 15
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 15

Cys Leu Val Lys Tyr Arg Ala Gln Val
1               5

<210> SEQ ID NO 16
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 16

His Thr Trp Pro His Ile Val Ala Ala
1               5

<210> SEQ ID NO 17
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 17

Lys Ile Phe Thr Phe Leu Tyr Gly Phe
1               5

<210> SEQ ID NO 18
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 18

Gly Leu Glu Asp Thr Leu Glu Gln Leu
1               5

<210> SEQ ID NO 19
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 19

His Ile Val Ala Ala Leu Val Trp Leu
1               5
```

```
<210> SEQ ID NO 20
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 20

Lys Leu Ala Arg Lys Leu Lys Leu Ile
1               5

<210> SEQ ID NO 21
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 21

Gly Ile Met His Asn Lys Leu Phe Leu
1               5

<210> SEQ ID NO 22
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 22

Ala Leu Ser Lys Ser Ser Met Tyr Thr
1               5

<210> SEQ ID NO 23
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 23

Leu Leu Glu Met Val Ala Thr His Val
1               5

<210> SEQ ID NO 24
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 24

Gly Ile Phe Ser Ser Ser Glu Lys Ile
1               5

<210> SEQ ID NO 25
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 25

Gln Leu Ala Glu Tyr His Lys Leu Ala
1               5
```

<210> SEQ ID NO 26
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 26

Phe Thr Phe Leu Tyr Gly Phe Leu Cys
1               5

<210> SEQ ID NO 27
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 27

Thr Gln Leu Ala Glu Tyr His Lys Leu
1               5

<210> SEQ ID NO 28
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 28

Val Gln Arg Glu Tyr Gln Leu Val Val
1               5

<210> SEQ ID NO 29
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 29

Tyr Gln Leu Val Val Gln Thr Thr Thr
1               5

<210> SEQ ID NO 30
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 30

Met Ile Thr Glu Ser Lys Arg Ser Val
1               5

<210> SEQ ID NO 31
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 31

Thr Leu Lys Glu Glu Val Gln Lys Leu
1               5

```
<210> SEQ ID NO 32
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 32

Ser Leu Glu Lys His Lys His Leu Leu
1               5

<210> SEQ ID NO 33
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 33

Thr Leu Glu Gln Leu Asn Ala Met Ile
1               5

<210> SEQ ID NO 34
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 34

Asn Leu Glu Ser His Ser Ala Ile Leu
1               5

<210> SEQ ID NO 35
<211> LENGTH: 9
<212> TYPE: PRT
<213> ORGANISM: Artificial Sequence
<220> FEATURE:
<223> OTHER INFORMATION: a peptide derived from KNTC2

<400> SEQUENCE: 35

Tyr Ser Val Ala Asp Ile Glu Arg Ile
1               5

<210> SEQ ID NO 36
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 36

Arg Leu Leu Glu Met Val Ala Thr His Val
1               5                   10

<210> SEQ ID NO 37
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 37

Phe Leu Tyr Gly Phe Leu Cys Pro Ser Tyr
1               5                   10

<210> SEQ ID NO 38
```

```
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 38

Tyr Met Ser Asn Leu Glu Ser His Ser Ala
1               5                   10

<210> SEQ ID NO 39
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 39

Lys Leu Trp Asn Glu Glu Leu Lys Tyr Ala
1               5                   10

<210> SEQ ID NO 40
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 40

Ala Leu Ser Lys Ser Ser Met Tyr Thr Val
1               5                   10

<210> SEQ ID NO 41
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 41

Lys Ile Phe Thr Phe Leu Tyr Gly Phe Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 42

Phe Leu Lys Ile Phe Thr Phe Leu Tyr Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 43

Asn Ile Ile Asp Asn Gln Lys Tyr Ser Val
1               5                   10

<210> SEQ ID NO 44
<211> LENGTH: 10
```

```
<212> TYPE: PRT
<213> ORGANISM: Artificial Sequence
<220> FEATURE:
<223> OTHER INFORMATION: a peptide derived from KNTC2

<400> SEQUENCE: 44

Ser Met Lys Ser Leu Gln Ala Pro Ser Val
1               5                   10

<210> SEQ ID NO 45
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 45

Ala Met Ile Thr Glu Ser Lys Arg Ser Val
1               5                   10

<210> SEQ ID NO 46
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 46

Glu Leu Leu Asn Glu Thr Glu Glu Glu Ile
1               5                   10

<210> SEQ ID NO 47
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 47

His Ile Val Ala Ala Leu Val Trp Leu Ile
1               5                   10

<210> SEQ ID NO 48
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 48

Trp Leu Ile Asp Cys Ile Lys Ile His Thr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 49

Phe Ala Leu Ser Lys Ser Ser Met Tyr Thr
1               5                   10

<210> SEQ ID NO 50
<211> LENGTH: 10
<212> TYPE: PRT
```

<213> ORGANISM: Artificial Sequence
<220> FEATURE:
<223> OTHER INFORMATION: a peptide derived from KNTC2

<400> SEQUENCE: 50

Cys Met Ser Glu Asp Leu Ser Glu Asn Ile
1               5                   10

<210> SEQ ID NO 51
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 51

Asp Leu Phe Asn Val Asp Ala Phe Lys Leu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 52

Lys Leu Asp Asp Leu Tyr Gln Gln Lys Ile
1               5                   10

<210> SEQ ID NO 53
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 53

Ala Ile Leu Asp Gln Lys Leu Asn Gly Leu
1               5                   10

<210> SEQ ID NO 54
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 54

Ser Met Gln Glu Leu Arg Ser Gln Asp Val
1               5                   10

<210> SEQ ID NO 55
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 55

Ala Ala Leu Val Trp Leu Ile Asp Cys Ile
1               5                   10

<210> SEQ ID NO 56
<211> LENGTH: 10
<212> TYPE: PRT
<213> ORGANISM: Artificial Sequence

```
<220> FEATURE:
<223> OTHER INFORMATION: a peptide derived from KNTC2

<400> SEQUENCE: 56

Leu Leu Glu Ser Thr Val Asn Gln Gly Leu
1               5                   10

<210> SEQ ID NO 57
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 57

Tyr Gly Phe Leu Cys Pro Ser Tyr Glu Leu
1               5                   10

<210> SEQ ID NO 58
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 58

Lys Leu Phe Leu Asp Tyr Thr Ile Lys Cys
1               5                   10

<210> SEQ ID NO 59
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 59

Arg Ala Leu Asn Glu Gln Ile Ala Arg Leu
1               5                   10

<210> SEQ ID NO 60
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 60

Phe Leu Asp Tyr Thr Ile Lys Cys Tyr Glu
1               5                   10

<210> SEQ ID NO 61
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 61

Glu Met Val Ala Thr His Val Gly Ser Val
1               5                   10

<210> SEQ ID NO 62
<211> LENGTH: 10
<212> TYPE: PRT
<213> ORGANISM: Artificial Sequence
<220> FEATURE:
```

<223> OTHER INFORMATION: a peptide derived from KNTC2

<400> SEQUENCE: 62

Phe Leu Cys Pro Ser Tyr Glu Leu Pro Asp
1               5                   10

<210> SEQ ID NO 63
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 63

Tyr Thr Ile Lys Cys Tyr Glu Ser Phe Met
1               5                   10

<210> SEQ ID NO 64
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 64

Lys Leu Lys Asp Leu Phe Asn Val Asp Ala
1               5                   10

<210> SEQ ID NO 65
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 65

Phe Thr Phe Leu Tyr Gly Phe Leu Cys Pro
1               5                   10

<210> SEQ ID NO 66
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 66

Asn Leu Gln Arg Leu Leu Glu Met Val Ala
1               5                   10

<210> SEQ ID NO 67
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 67

Ser Met Tyr Thr Val Gly Ala Pro His Thr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: a peptide derived from KNTC2

```
<400> SEQUENCE: 68

Leu Val Trp Leu Ile Asp Cys Ile Lys Ile
1               5                   10

<210> SEQ ID NO 69
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 69

His Thr Trp Pro His Ile Val Ala Ala Leu
1               5                   10

<210> SEQ ID NO 70
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 70

Phe Lys Asp Leu Gly Tyr Pro Phe Ala Leu
1               5                   10

<210> SEQ ID NO 71
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 71

Asn Val Asp Ala Phe Lys Leu Glu Ser Leu
1               5                   10

<210> SEQ ID NO 72
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 72

Phe Met Ser Gly Ala Asp Ser Phe Asp Glu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 73

Ile Met His Asn Lys Leu Phe Leu Asp Tyr
1               5                   10

<210> SEQ ID NO 74
<211> LENGTH: 10
<212> TYPE: PRT
<213> ORGANISM: Artificial Sequence
<220> FEATURE:
<223> OTHER INFORMATION: a peptide derived from KNTC2
```

<400> SEQUENCE: 74

Lys Leu Asn Gly Leu Asn Glu Glu Ile Ala
1               5                   10

<210> SEQ ID NO 75
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 75

Lys Leu Lys Ala Ser Leu Gln Gly Asp Val
1               5                   10

<210> SEQ ID NO 76
<211> LENGTH: 10
<212> TYPE: PRT
<213> ORGANISM: Artificial Sequence
<220> FEATURE:
<223> OTHER INFORMATION: a peptide derived from KNTC2

<400> SEQUENCE: 76

Asn Asn Leu Gln Arg Leu Leu Glu Met Val
1               5                   10

<210> SEQ ID NO 77
<211> LENGTH: 2209
<212> TYPE: DNA
<213> ORGANISM: Homo sapiens

<400> SEQUENCE: 77

```
actgcgcgcg tcgtgcgtaa tgacgtcagc gccggcggag aatttcaaat tcgaacggct      60
ttggcgggcc gaggaaggac ctggtgtttt gatgaccgct gtcctgtcta gcagatactt     120
gcacggttta cagaaattcg gtccctgggt cgtgtcagga actggaaaa aaggtcataa     180
gcatgaagcg cagttcagtt ccagcggtg gtgctggccg cctctccatg caggagttaa     240
gatcccagga tgtaaataaa caaggcctct atacccctca aaccaaagag aaaccaacct     300
ttggaaagtt gagtataaac aaaccgacat ctgaaagaaa agtctcgcta tttggcaaaa     360
gaactagtgg acatggatcc cggaatagtc aacttggtat attttccagt tctgagaaaa     420
tcaaggaccc gagaccactt aatgacaaag cattcattca gcagtgtatt cgacaactct     480
gtgagtttct tacagaaaat ggttatgcac ataatgtgtc catgaaatct ctacaagctc     540
cctctgttaa agacttcctg aagatcttca catttcttta tggcttcctg tgcccctcat     600
acgaacttcc tgacacaaag tttgaagaag aggttccaag aatctttaaa gaccttgggt     660
atcctttgc actatccaaa agctccatgt acacagtggg ggctcctcat acatggcctc     720
acattgtggc agccttagtt tggctaatag actgcatcaa gatacatact gccatgaaag     780
aaagctcacc tttatttgat gatgggcagc cttggggaga gaaactgaa gatgaaatta     840
tgcataataa gttgtttttg gactacacca taaaatgcta tgagagtttt atgagtggtg     900
ccgacagctt tgatgagatg aatgcagagc tgcagtcaaa actgaaggat ttatttaatg     960
tggatgcttt taagctggaa tcattagaag caaaaaacag agcattgaat gaacagattg    1020
caagattgga acaagaaaga gaaaagaac cgaatcgtct agagtcgttg agaaaactga    1080
aggcttcctt acaaggagat gttcaaaagt atcaggcata catgagcaat ttggagtctc    1140
attcagccat tcttgaccag aaaattaatg gtctcaatga ggaaattgct agagtagaac    1200
```

```
tagaatgtga acaataaaa caggagaaca ctcgactaca gaatatcatt gacaaccaga    1260
agtactcagt tgcagacatt gagcgaataa atcatgaaag aaatgaattg cagcagacta    1320
ttaataaatt aaccaaggac ctggaagctg aacaacagaa gttgtggaat gaggagttaa    1380
aatatgccag aggcaaagaa gcgattgaaa cacaattagc agagtatcac aaattggcta    1440
gaaaattaaa acttattcct aaaggtgctg agaattccaa aggttatgac tttgaaatta    1500
agtttaatcc cgaggctggt gccaactgcc ttgtcaaata cagggctcaa gtttatgtac    1560
ctcttaagga actcctgaat gaaactgaag aagaaattaa taaagcccta aataaaaaaa    1620
tgggtttgga ggatacttta gaacaattga atgcaatgat aacagaaagc aagagaagtg    1680
tgagaactct gaagaagaa gttcaaaagc tggatgatct ttaccaacaa aaaattaagg    1740
aagcagagga agaggatgaa aaatgtgcca gtgagcttga gtccttggag aaacacaagc    1800
acctgctaga aagtactgtt aaccagggc tcagtgaagc tatgaatgaa ttagatgctg    1860
ttcagcggga ataccaacta gttgtgcaaa ccacgactga agaaagacga aaagtgggaa    1920
ataacttgca acgtctgtta gagatggttg ctacacatgt tgggtctgta gagaaacatc    1980
ttgaggagca gattgctaaa gttgatagag aatatgaaga atgcatgtca gaagatctct    2040
cggaaaatat taaagagatt agagataagt atgaagaaga agctactcta attaagtctt    2100
ctgaagaatg aagataaaat gttgatcatg tatatatatc catagtgaat aaaattgtct    2160
cagtaaagtg taaaaaaaaa aaaaaaaaaa aaaaaaaaa aaaaaaaaa                 2209
```

```
<210> SEQ ID NO 78
<211> LENGTH: 2150
<212> TYPE: DNA
<213> ORGANISM: Homo sapiens
<220> FEATURE:
<221> NAME/KEY: CDS
<222> LOCATION: (105)..(2033)

<400> SEQUENCE: 78
ctcgagccac gaaggccccg ctgtcctgtc tagcagatac ttgcacggtt tacagaaatt     60
cggtccctgg gtcgtgtcag gaaactggaa aaaaggtcat aagc atg aag cgc agt    116
                                                Met Lys Arg Ser
                                                  1 tca gtt tcc agc ggt ggt gct ggc cgc ctc tcc atg cag gag tta aga    164
Ser Val Ser Ser Gly Gly Ala Gly Arg Leu Ser Met Gln Glu Leu Arg
  5                  10                  15                  20 tcc cag gat gta aat aaa caa ggc ctc tat acc cct caa acc aaa gag    212
Ser Gln Asp Val Asn Lys Gln Gly Leu Tyr Thr Pro Gln Thr Lys Glu
                 25                  30                  35 aaa cca acc ttt gga aag ttg agt ata aac aaa ccg aca tct gaa aga    260
Lys Pro Thr Phe Gly Lys Leu Ser Ile Asn Lys Pro Thr Ser Glu Arg
         40                  45                  50 aaa gtc tcg cta ttt ggc aaa aga act agt gga cat gga tcc cgg aat    308
Lys Val Ser Leu Phe Gly Lys Arg Thr Ser Gly His Gly Ser Arg Asn
     55                  60                  65 agt caa ctt ggt ata ttt tcc agt tct gag aaa atc aag gac ccg aga    356
Ser Gln Leu Gly Ile Phe Ser Ser Ser Glu Lys Ile Lys Asp Pro Arg
 70                  75                  80 cca ctt aat gac aaa gca ttc att cag cag tgt att cga caa ctc tgt    404
Pro Leu Asn Asp Lys Ala Phe Ile Gln Gln Cys Ile Arg Gln Leu Cys
 85                  90                  95                 100 gag ttt ctt aca gaa aat ggt tat gca cat aat gtg tcc atg aaa tct    452
Glu Phe Leu Thr Glu Asn Gly Tyr Ala His Asn Val Ser Met Lys Ser
                105                 110                 115
```

```
cta caa gct ccc tct gtt aaa gac ttc ctg aag atc ttc aca ttt ctt      500
Leu Gln Ala Pro Ser Val Lys Asp Phe Leu Lys Ile Phe Thr Phe Leu
            120                 125                 130 tat ggc ttc ctg tgc ccc tca tac gaa ctt cct gac aca aag ttt gaa      548
Tyr Gly Phe Leu Cys Pro Ser Tyr Glu Leu Pro Asp Thr Lys Phe Glu
        135                 140                 145 gaa gag gtt cca aga atc ttt aaa gac ctt ggg tat cct ttt gca cta      596
Glu Glu Val Pro Arg Ile Phe Lys Asp Leu Gly Tyr Pro Phe Ala Leu
    150                 155                 160 tcc aaa agc tcc atg tac aca gtg ggg gct cct cat aca tgg cct cac      644
Ser Lys Ser Ser Met Tyr Thr Val Gly Ala Pro His Thr Trp Pro His
165                 170                 175                 180 att gtg gca gcc tta gtt tgg cta ata gac tgc atc aag ata cat act      692
Ile Val Ala Ala Leu Val Trp Leu Ile Asp Cys Ile Lys Ile His Thr
                185                 190                 195 gcc atg aaa gaa agc tca cct tta ttt gat gat ggg cag cct tgg gga      740
Ala Met Lys Glu Ser Ser Pro Leu Phe Asp Asp Gly Gln Pro Trp Gly
            200                 205                 210 gaa gaa act gaa gat gga att atg cat aat aag ttg ttt ttg gac tac      788
Glu Glu Thr Glu Asp Gly Ile Met His Asn Lys Leu Phe Leu Asp Tyr
        215                 220                 225 acc ata aaa tgc tat gag agt ttt atg agt ggt gcc gac agc ttt gat      836
Thr Ile Lys Cys Tyr Glu Ser Phe Met Ser Gly Ala Asp Ser Phe Asp
230                 235                 240 gag atg aat gca gag ctg cag tca aaa ctg aag gat tta ttt aat gtg      884
Glu Met Asn Ala Glu Leu Gln Ser Lys Leu Lys Asp Leu Phe Asn Val
245                 250                 255                 260 gat gct ttt aag ctg gaa tca tta gaa gca aaa aac aga gca ttg aat      932
Asp Ala Phe Lys Leu Glu Ser Leu Glu Ala Lys Asn Arg Ala Leu Asn
                265                 270                 275 gaa cag att gca aga ttg gaa caa gaa aga gaa aaa gaa ccg aat cgt      980
Glu Gln Ile Ala Arg Leu Glu Gln Glu Arg Glu Lys Glu Pro Asn Arg
            280                 285                 290 cta gag tcg ttg aga aaa ctg aag gct tcc tta caa gga gat gtt caa     1028
Leu Glu Ser Leu Arg Lys Leu Lys Ala Ser Leu Gln Gly Asp Val Gln
        295                 300                 305 aag tat cag gca tac atg agc aat ttg gag tct cat tca gcc att ctt     1076
Lys Tyr Gln Ala Tyr Met Ser Asn Leu Glu Ser His Ser Ala Ile Leu
310                 315                 320 gac cag aaa tta aat ggt ctc aat gag gaa att gct aga gta gaa cta     1124
Asp Gln Lys Leu Asn Gly Leu Asn Glu Glu Ile Ala Arg Val Glu Leu
325                 330                 335                 340 gaa tgt gaa aca ata aaa cag gag aac act cga cta cag aat atc att     1172
Glu Cys Glu Thr Ile Lys Gln Glu Asn Thr Arg Leu Gln Asn Ile Ile
                345                 350                 355 gac aac cag aag tac tca gtt gca gac att gag cga ata aat cat gaa     1220
Asp Asn Gln Lys Tyr Ser Val Ala Asp Ile Glu Arg Ile Asn His Glu
            360                 365                 370 aga aat gaa ttg cag cag act att aat aaa tta acc aag gac ctg gaa     1268
Arg Asn Glu Leu Gln Gln Thr Ile Asn Lys Leu Thr Lys Asp Leu Glu
        375                 380                 385 gct gaa caa cag aag ttg tgg aat gag gag tta aaa tat gcc aga ggc     1316
Ala Glu Gln Gln Lys Leu Trp Asn Glu Glu Leu Lys Tyr Ala Arg Gly
390                 395                 400 aaa gaa gcg att gaa aca caa tta gca gag tat cac aaa ttg gct aga     1364
Lys Glu Ala Ile Glu Thr Gln Leu Ala Glu Tyr His Lys Leu Ala Arg
405                 410                 415                 420 aaa tta aaa ctt att cct aaa ggt gct gag aat tcc aaa ggt tat gac     1412
Lys Leu Lys Leu Ile Pro Lys Gly Ala Glu Asn Ser Lys Gly Tyr Asp
                425                 430                 435
```

```
ttt gaa att aag ttt aat ccc gag gct ggt gcc aac tgc ctt gtc aaa      1460
Phe Glu Ile Lys Phe Asn Pro Glu Ala Gly Ala Asn Cys Leu Val Lys
            440                 445                 450 tac agg gct caa gtt tat gta cct ctt aag gaa ctc ctg aat gaa act      1508
Tyr Arg Ala Gln Val Tyr Val Pro Leu Lys Glu Leu Leu Asn Glu Thr
455                 460                 465 gaa gaa gaa att aat aaa gcc cta aat aaa aaa atg ggt ttg gag gat      1556
Glu Glu Glu Ile Asn Lys Ala Leu Asn Lys Lys Met Gly Leu Glu Asp
        470                 475                 480 act tta gaa caa ttg aat gca atg ata aca gaa agc aag aga agt gtg      1604
Thr Leu Glu Gln Leu Asn Ala Met Ile Thr Glu Ser Lys Arg Ser Val
485                 490                 495                 500 aga act ctg aaa gaa gaa gtt caa aag ctg gat gat ctt tac caa caa      1652
Arg Thr Leu Lys Glu Glu Val Gln Lys Leu Asp Asp Leu Tyr Gln Gln
                505                 510                 515 aaa att aag gaa gca gag gaa gag gat gaa aaa tgt gcc agt gag ctt      1700
Lys Ile Lys Glu Ala Glu Glu Glu Asp Glu Lys Cys Ala Ser Glu Leu
            520                 525                 530 gag tcc ttg gag aaa cac aag cac ctg cta gaa agt act gtt aac cag      1748
Glu Ser Leu Glu Lys His Lys His Leu Leu Glu Ser Thr Val Asn Gln
        535                 540                 545 ggg ctc agt gaa gct atg aat gaa tta gat gct gtt cag cgg gaa tac      1796
Gly Leu Ser Glu Ala Met Asn Glu Leu Asp Ala Val Gln Arg Glu Tyr
550                 555                 560 caa cta gtt gtg caa acc acg act gaa gaa aga cga aaa gtg gga aat      1844
Gln Leu Val Val Gln Thr Thr Thr Glu Glu Arg Arg Lys Val Gly Asn
565                 570                 575                 580 aac ttg caa cgt ctg tta gag atg gtt gct aca cat gtt ggg tct gta      1892
Asn Leu Gln Arg Leu Leu Glu Met Val Ala Thr His Val Gly Ser Val
                585                 590                 595 gag aaa cat ctt gag gag cag att gct aaa gtt gat aga gaa tat gaa      1940
Glu Lys His Leu Glu Glu Gln Ile Ala Lys Val Asp Arg Glu Tyr Glu
            600                 605                 610 gaa tgc atg tca gaa gat ctc tcg gaa aat att aaa gag att aga gat      1988
Glu Cys Met Ser Glu Asp Leu Ser Glu Asn Ile Lys Glu Ile Arg Asp
        615                 620                 625 aag tat gag aag aaa gct act cta att aag tct tct gaa gaa tga          2033
Lys Tyr Glu Lys Lys Ala Thr Leu Ile Lys Ser Ser Glu Glu
            630                 635                 640 agataaaatg ttgatcatgt atatatatcc atagtgaata aaattgtctc agtaaaaaaa    2093
aaaaaaaaaa aaaaaaaaaa aaaaaaaaaa aaaaaaaaaa aaaaaaaaaa aaaaaaa       2150

<210> SEQ ID NO 79
<211> LENGTH: 642
<212> TYPE: PRT
<213> ORGANISM: Homo sapiens

<400> SEQUENCE: 79

Met Lys Arg Ser Ser Val Ser Ser Gly Gly Ala Gly Arg Leu Ser Met
1               5                   10                  15

Gln Glu Leu Arg Ser Gln Asp Val Asn Lys Gln Gly Leu Tyr Thr Pro
            20                  25                  30

Gln Thr Lys Glu Lys Pro Thr Phe Gly Lys Leu Ser Ile Asn Lys Pro
        35                  40                  45

Thr Ser Glu Arg Lys Val Ser Leu Phe Gly Lys Arg Thr Ser Gly His
    50                  55                  60

Gly Ser Arg Asn Ser Gln Leu Gly Ile Phe Ser Ser Glu Lys Ile
65                  70                  75                  80
```

-continued

```
Lys Asp Pro Arg Pro Leu Asn Asp Lys Ala Phe Ile Gln Gln Cys Ile
                 85                  90                  95

Arg Gln Leu Cys Glu Phe Leu Thr Glu Asn Gly Tyr Ala His Asn Val
            100                 105                 110

Ser Met Lys Ser Leu Gln Ala Pro Ser Val Lys Asp Phe Leu Lys Ile
        115                 120                 125

Phe Thr Phe Leu Tyr Gly Phe Leu Cys Pro Ser Tyr Glu Leu Pro Asp
    130                 135                 140

Thr Lys Phe Glu Glu Val Pro Arg Ile Phe Lys Asp Leu Gly Tyr
145                 150                 155                 160

Pro Phe Ala Leu Ser Lys Ser Ser Met Tyr Thr Val Gly Ala Pro His
                165                 170                 175

Thr Trp Pro His Ile Val Ala Ala Leu Val Trp Leu Ile Asp Cys Ile
                180                 185                 190

Lys Ile His Thr Ala Met Lys Glu Ser Ser Pro Leu Phe Asp Asp Gly
            195                 200                 205

Gln Pro Trp Gly Glu Glu Thr Glu Asp Gly Ile Met His Asn Lys Leu
        210                 215                 220

Phe Leu Asp Tyr Thr Ile Lys Cys Tyr Glu Ser Phe Met Ser Gly Ala
225                 230                 235                 240

Asp Ser Phe Asp Glu Met Asn Ala Glu Leu Gln Ser Lys Leu Lys Asp
                245                 250                 255

Leu Phe Asn Val Asp Ala Phe Lys Leu Glu Ser Leu Glu Ala Lys Asn
            260                 265                 270

Arg Ala Leu Asn Glu Gln Ile Ala Arg Leu Glu Gln Glu Arg Glu Lys
        275                 280                 285

Glu Pro Asn Arg Leu Glu Ser Leu Arg Lys Leu Lys Ala Ser Leu Gln
    290                 295                 300

Gly Asp Val Gln Lys Tyr Gln Ala Tyr Met Ser Asn Leu Glu Ser His
305                 310                 315                 320

Ser Ala Ile Leu Asp Gln Lys Leu Asn Gly Leu Asn Glu Glu Ile Ala
                325                 330                 335

Arg Val Glu Leu Glu Cys Glu Thr Ile Lys Gln Glu Asn Thr Arg Leu
            340                 345                 350

Gln Asn Ile Ile Asp Asn Gln Lys Tyr Ser Val Ala Asp Ile Glu Arg
        355                 360                 365

Ile Asn His Glu Arg Asn Glu Leu Gln Gln Thr Ile Asn Lys Leu Thr
    370                 375                 380

Lys Asp Leu Glu Ala Glu Gln Gln Lys Leu Trp Asn Glu Glu Leu Lys
385                 390                 395                 400

Tyr Ala Arg Gly Lys Glu Ala Ile Glu Thr Gln Leu Ala Glu Tyr His
                405                 410                 415

Lys Leu Ala Arg Lys Leu Lys Leu Ile Pro Lys Gly Ala Glu Asn Ser
            420                 425                 430

Lys Gly Tyr Asp Phe Glu Ile Lys Phe Asn Pro Glu Ala Gly Ala Asn
        435                 440                 445

Cys Leu Val Lys Tyr Arg Ala Gln Val Tyr Val Pro Leu Lys Glu Leu
    450                 455                 460

Leu Asn Glu Thr Glu Glu Ile Asn Lys Ala Leu Asn Lys Lys Met
465                 470                 475                 480

Gly Leu Glu Asp Thr Leu Glu Gln Leu Asn Ala Met Ile Thr Glu Ser
                485                 490                 495
```

```
Lys Arg Ser Val Arg Thr Leu Lys Glu Val Gln Lys Leu Asp Asp
            500                 505                 510
Leu Tyr Gln Gln Lys Ile Lys Glu Ala Glu Glu Asp Glu Lys Cys
        515                 520                 525
Ala Ser Glu Leu Glu Ser Leu Glu Lys His Lys His Leu Leu Glu Ser
530                 535                 540
Thr Val Asn Gln Gly Leu Ser Glu Ala Met Asn Glu Leu Asp Ala Val
545                 550                 555                 560
Gln Arg Glu Tyr Gln Leu Val Val Gln Thr Thr Glu Glu Arg Arg
                565                 570                 575
Lys Val Gly Asn Asn Leu Gln Arg Leu Leu Glu Met Val Ala Thr His
            580                 585                 590
Val Gly Ser Val Glu Lys His Leu Glu Glu Gln Ile Ala Lys Val Asp
                595                 600                 605
Arg Glu Tyr Glu Glu Cys Met Ser Glu Asp Leu Ser Glu Asn Ile Lys
        610                 615                 620
Glu Ile Arg Asp Lys Tyr Glu Lys Lys Ala Thr Leu Ile Lys Ser Ser
625                 630                 635                 640
Glu Glu
```

```
<210> SEQ ID NO 80
<211> LENGTH: 22
<212> TYPE: DNA
<213> ORGANISM: Artificial Sequence
<220> FEATURE:
<223> OTHER INFORMATION: a PCR primer for the TCR analysis

<400> SEQUENCE: 80
gtctaccagg cattcgcttc at                                         22

<210> SEQ ID NO 81
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 81
tcagctggac cacagccgca gcgt                                       24

<210> SEQ ID NO 82
<211> LENGTH: 21
<212> TYPE: DNA
<213> ORGANISM: Artificial Sequence
<220> FEATURE:
<223> OTHER INFORMATION: a PCR primer for the TCR analysis

<400> SEQUENCE: 82
tcagaaatcc tttctcttga c                                          21

<210> SEQ ID NO 83
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 83
ctagcctctg gaatcctttc tctt                                       24

<210> SEQ ID NO 84
```

```
<211> LENGTH: 4
<212> TYPE: PRT
<213> ORGANISM: Artificial Sequence
<220> FEATURE:
<223> OTHER INFORMATION: An artificially synthesized peptide sequence

<400> SEQUENCE: 84

Asn Lys Arg Lys
1
```

KNTC2 PEPTIDES AND VACCINES CONTAINING THE SAME

TECHNICAL FIELD

The present invention relates to the field of biological science, more specifically to the field of cancer therapy. In particular, the present invention relates to novel peptides that are effective as cancer vaccines, as well as drugs for either or both of the treatment and/or prophylaxis of tumors.

CROSS-REFERENCES TO RELATED APPLICATIONS

The present application is a National Stage of International Application No. PCT/JP2014/001350, filed Mar. 11, 2014, and which claims the benefit of U.S. Provisional Application No. 61/777,334, filed on Mar. 12, 2013, the entire contents of which are incorporated by reference herein.

REFERENCE TO SEQUENCE LISTING

This application includes a Sequence Listing as a text file named "87331-956347-SEQLIST.txt" created Aug. 20, 2015, and containing 35,307 bytes. The material contained in this text file is incorporated by reference in its entirety for all purposes.

BACKGROUND ART

CD8 positive cytotoxic T lymphocytes (CTLs) have been shown to recognize epitope peptides derived from the tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered, primarily through immunological approaches (NPL 1-2). Some of these TAAs are currently undergoing clinical development as immunotherapeutic targets.

Favorable TAAs are indispensable for the proliferation and survival of cancer cells. The use of such TAAs as targets for immunotherapy may minimize the well-described risk of immune escape of cancer cells attributable to deletion, mutation, or downregulation of TAAs as a consequence of therapeutically driven immune selection. Accordingly, the identification of new TAAs capable of inducing potent and specific anti-tumor immune responses warrants further development. Thus, the clinical application of peptide vaccination strategies for various types of cancer is ongoing (NPL 3-10). To date, there have been several reports of clinical trials using these TAA derived peptides. Unfortunately, these cancer vaccine trials have to date yielded only a low objective response rate (NPL 11-13). Accordingly, there remains a need for new TAAs as immunotherapeutic targets.

KNTC2, also known as "kinetchore associated 2", HEC1 or NDC 80, is a member of the Ndc80 complex that is composed of the two subcomplexes of Ndc80 (KNTC2)-Nuf2 (CDCA1) and Spc24-Spc25 (NPL 14). The attachment sites of the CDCA1-KNTC2 complex within the kinetochore outer plate generate microtubule dependent forces for chromosomal movement and regulate spindle checkpoint protein assembly at the kinetochore (NPL 15).

In the course of clarifying the molecular mechanism in non-small cell lung cancer (NSCLC) by genome-wide expression profile analysis using cDNA microarray containing 27,648 genes, KNTC2 was discovered to be frequently over expressed in NSCLC (NPL 16, 17, 18, 19, 20). Northern blot analyses revealed this gene transcript to be highly expressed in lung cancer tissues but not expressed in normal tissues, with the exception of the testis. Moreover, subsequent knockdown of KNTC2 expression with siRNA was shown to significantly suppress growth of NSCLC cells (NPL 21, PTL 1).

KNTC2 has also been reported to be up-regulated in tissues of cancers, such as bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor (PTL 2).

In addition, the present inventors have identified a KNTC2 peptide that can bind to HLA-A24 and induce CTLs, and that is useful for an immunotherapy that targets HLA-A24 positive patients (PTL 2). However, although these peptides may be suitable for patients expressing the HLA-A24 subtype, there remains a need for peptides that induce CTL in patients expressing other types of HLA antigen.

CITATION LIST

Patent Literature

[PTL 1] WO2007/013480
[PTL 2] WO2008/102557

Non Patent Literature

[NPL 1] Boon T, Int J Cancer 1993, 54(2): 177-80
[NPL 2] Boon T & van der Bruggen P, J Exp Med 1996, 183(3): 725-9
[NPL 3] Harris C C, J Natl Cancer Inst 1996, 88(20): 1442-55
[NPL 4] Butterfield L H et al., Cancer Res 1999, 59(13): 3134-42
[NPL 5] Vissers J L et al., Cancer Res 1999, 59(21): 5554-9
[NPL 6] van der Burg S H et al., J Immunol 1996, 156(9): 3308-14
[NPL 7] Tanaka F et al., Cancer Res 1997, 57(20): 4465-8
[NPL 8] Fujie T et al., Int J Cancer 1999, 80(2): 169-72
[NPL 9] Kikuchi M et al., Int J Cancer 1999, 81(3): 459-66
[NPL 10] Oiso M et al., Int J Cancer 1999, 81(3): 387-94
[NPL 11] Belli F et al., J Clin Oncol 2002, 20(20): 4169-80
[NPL 12] Coulie P G et al., Immunol Rev 2002, 188: 33-42
[NPL 13] Rosenberg S A et al., Nat Med 2004, 10(9): 909-15
[NPL 14] Ciferri C, et al. J Biol Chem 2005; 280: 29088-95
[NPL 15] Wigge P. A, et al. J Cell Biol. 2001; 152: 349-60
[NPL 16] Kikuchi T, et al., Oncogene. 2003; 22:2192-205
[NPL 17] Suzuki C, et al., Cancer Res. 2003; 63:7038-41
[NPL 18] Kakiuchi S, et al., Mol Cancer Res. 2003; 1:485-99
[NPL 19] Zembutsu H, et al., Int J. Oncol. 2003; 23:29-39
[NPL 20] Kakiuchi S, et al., Hum Mol Genet. 2004; 13:3029-43
[NPL 21] Hayama S, et al. Cancer Res. 2006 Nov. 1; 66(21):10339-48

SUMMARY OF INVENTION

The present invention is based, at least in part, on the discovery of novel peptides that may serve as suitable targets of immunotherapy. Because TAAs are generally perceived by the immune system as "self" and therefore often have no innate immunogenicity, the discovery of appropriate targets is still of importance. In the course of the present invention, KNTC2 (a typical amino acid sequence shown in SEQ ID NO: 79; a typical nucleotide sequence shown in SEQ ID NO: 77 (GenBank Accession No. NM_006101) or SEQ ID NO 78 (GenBank Accession No. AF017790)) is demonstrated to be specifically over-expressed in cancers, examples of which include, but are not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor. Thus, the present invention focuses on KNTC2 as a candidate target for cancer/tumor immunotherapy.

To that end, the present invention is directed, at least in part, to the identification of specific epitope peptides that possess the ability to induce cytotoxic T lymphocytes (CTLs) specific to KNTC2 among peptides derived from KNTC2.

The results disclosed herein demonstrate that identified peptides are HLA-A2 restricted epitope peptides that can induce potent and specific immune responses against cells expressing KNTC2.

Accordingly, it is an object of the present invention to provide KNTC2-derived peptides that can be used to induce CTLs in vitro, ex vivo or in vivo in HLA-A2 restricted manner, or to be directly administered to a subject so as to induce in vivo immune responses against cancers, examples of which include, but are not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor.

The peptides of the present invention are generally less than 15, 14, 13, 12, 11, or 10 amino acids in length. Preferred peptides are nonapeptides and decapeptides. Particularly preferred nonapeptides and decapeptides have an amino acid sequence selected from among SEQ ID NOs: 2, 3, 7, 17, 41, 53 and 68.

The present invention also contemplates modified peptides having an amino acid sequence in which one, two or more amino acids are substituted, deleted, inserted and/or added to an amino acid sequence selected from among SEQ ID NOs: 2, 3, 7, 17, 41, 53 and 68, provided the resulting modified peptides retain the requisite CTL inducibility of the original unmodified peptide.

In one embodiment, when the original peptide is a 9-mer (e.g., one of SEQ ID NOs: 2, 3, 7, and 17), the size of the modified peptide is preferably in the range of 9 to 40 amino acids, such as in the range of 9 to 20 amino acids, for example in the range of 9 to 15 amino acids. Likewise, when the original peptide is a 10-mer (e.g., one of SEQ ID NOs: 41, 53 and 68), the size of the modified peptide is preferably in the range of 10 to 40 amino acids, such as in the range of 10 to 20 amino acids, for example in the range of 10 to 15 amino acids.

The present invention further encompasses isolated polynucleotides encoding any one of the peptides of the present invention. These polynucleotides can be used to induce or prepare antigen presenting cells (APCs) having CTL inducibility. Like the peptides of the present invention, such APCs can be administered to a subject so as to induce an immune response against a cancer.

When administered to a subject, the peptides of the present invention can be presented on the surface of APCs so as to induce CTLs targeting the respective peptides. Therefore, one object of the present invention is to provide agents or compositions including one or more peptides of the present invention, or one or more polynucleotides encoding such peptides. The composition of the present invention may be used to induce a CTL and thus find utility in the treatment and/or prophylaxis of a cancer, and/or the prevention of a metastasis or post-operative recurrence thereof. Examples of targeted cancers contemplated by the present invention include, but are not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor.

The present invention further contemplates pharmaceutical compositions that include one or more peptides or polynucleotides of the present invention. The pharmaceutical composition is preferably formulated for use in the treatment and/or prophylaxis of a cancer, more particularly a primary cancer, and/or prevention of metastatic or post-operative recurrence thereof. Instead of or in addition to the peptides or polynucleotides of the present invention, the pharmaceutical compositions of the present invention may include as active ingredients APCs or exosomes that present any of the peptides of the present invention.

The peptides or polynucleotides of the present invention may be used to induce APCs that present on the surface a complex of a human leukocyte antigen (HLA) and a peptide of the present invention, for example, by contacting APCs derived from a subject with a peptide of the present invention or by introducing a polynucleotide encoding a peptide of the present invention into APCs. Such APCs have the ability to induce CTLs that specifically recognize cells that present target peptides on the surface and thus are useful in the context of cancer immunotherapy. Accordingly, the present invention encompasses the methods for inducing APCs with CTL inducibility as well as the APCs obtained by such methods.

In addition, the present invention also encompasses compositions that induce APCs having CTL inducibility, such compositions including any peptides or polynucleotides of the present invention.

It is a further object of the present invention to provide methods for inducing CTLs, such methods including the step of co-culturing CD8 positive T cells with APCs presenting on its surface a complex of an HLA antigen and a peptide of the present invention, the step of co-culturing CD8 positive T cells with exosomes presenting on its surface a complex of an HLA antigen and a peptide of the present invention, or the step of introducing a polynucleotide encoding both of T cell receptor (TCR) subunits or polynucleotides encoding each of TCR subunits, wherein the TCR can bind to a complex of the peptide of the present invention and an HLA antigen presented on cell surface. CTLs obtained by such methods can find use in the treatment and/or prevention of cancers, examples of which include, but are not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor. Accordingly, the present invention encompasses both the methods for inducing CTLs and the CTLs obtained by such methods.

Yet another object of the present invention is to provide isolated APCs that present on the surface a complex of an HLA antigen and a peptide of the present invention. The present invention further provides isolated CTLs that target peptides of the present invention. Such CTLs may be also defined as CTLs that can recognize (or bind to) a complex of a peptide of the present invention and an HLA antigen on the cell surface. These APCs and CTLs find utility in the context of cancer immunotherapy.

It is yet another object of the present invention to provide methods for inducing an immune response against a cancer in a subject in need thereof, such methods including the step of administering to the subject a composition that includes at least one component selected from among (a) a peptide of the present invention or a polynucleotide encoding such a peptide, (b) an APC or exosome presenting such peptide(s) and (c) a CTL that can recognize a cell presenting a peptide of the present invention on its surface.

One aspect of the present invention pertains to a peptide of the present invention, an agent or composition containing such a peptide for use as a medicament.

The applicability of the present invention extends to any of a number of diseases relating to or arising from KNTC2 overexpression, such as cancer, examples of which include, but are not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor.

More specifically, the present invention provides followings:

[1] An isolated peptide having cytotoxic T lymphocyte (CTL) inducibility, wherein the peptide comprises an amino acid sequence (a) or (b) bellow:
  (a) an amino acid sequence of an immunologically active fragment of KNTC2;
  (b) an amino acid sequence in which 1, 2, or several amino acid(s) are substituted, deleted, inserted and/or added in an amino acid sequence of an immunologically active fragment of KNTC2,
  wherein the CTL induced by the peptide has specific cytotoxic activity against a cell that presents a fragment derived from KNTC2;

[2] The peptide of [1], wherein the peptide comprises an amino acid sequence (a) or (b) bellow:
  (a) an amino acid sequence selected from the group consisting of SEQ ID NOs: 2, 3, 7, 17, 41, 53 and 68;
  (b) an amino acid sequence in which 1, 2, or several amino acid(s) are substituted, deleted, inserted and/or added in the amino acid sequence selected from the group consisting of SEQ ID NOs: 2, 3, 7, 17, 41, 53 and 68;

[3] The peptide of [2], wherein the peptide has one or both of the following characteristics:
  (a) the second amino acid from the N-terminus is leucine or methionine; and
  (b) the C-terminal amino acid is valine or leucine;

[4] The peptide of any one of [1] to [3], wherein the peptide is a nonapeptide or a decapeptide;

[5] The peptide of [4], wherein the peptide consists of the amino acid sequence selected from the group consisting of SEQ ID NOs: 2, 3, 7, 17, 41, 53 and 68.

[6] An isolated polynucleotide encoding the peptide of any one of [1] to [5];

[7] A composition for inducing a CTL, wherein the composition comprises at least one active ingredient selected from the group consisting of:
  (a) the peptide of any one of [1] to [5];
  (b) the polynucleotide of [6];
  (c) an antigen-presenting cell (APC) that presents the peptide of any one of [1] to [5] on its surface; and
  (d) an exosome that presents the peptide of any one of [1] to [5] on its surface;

[8] A pharmaceutical composition for the treatment and/or prophylaxis of cancer, and/or the prevention of a postoperative recurrence thereof, wherein the composition comprises at least one active ingredient selected from the group consisting of:
  (a) the peptide of any one of [1] to [5];
  (b) the polynucleotide of [6];
  (c) an APC that presents the peptide of any one of [1] to [5] on its surface;
  (d) an exosome that presents the peptide of any one of [1] to [5] on its surface; and
  (e) a CTL that can recognize a cell presenting the peptide of any one of [1] to [5];

[9] The pharmaceutical composition of [8], wherein the pharmaceutical composition is formulated for the administration to a subject whose HLA antigen is HLA-A2;

[10] A method for inducing an APC with CTL inducibility, wherein the method comprises the step selected from the group consisting of:
  (a) contacting an APC with the peptide of any one of [1] to [5], and
  (b) introducing a polynucleotide encoding the peptide of any one of [1] to [5] into an APC;

[11] A method for inducing a CTL, wherein the method comprises a step selected from the group consisting of:
  (a) co-culturing a CD8 positive T cell with an APC that presents on its surface a complex of an HLA antigen and the peptide of any one of [1] to [5];
  (b) co-culturing a CD8 positive T cell with an exosome that presents on its surface a complex of an HLA antigen and the peptide of any one of [1] to [5]; and
  (c) introducing into a CD8 positive T cell a polynucleotide encoding both of T cell receptor (TCR) subunits or polynucleotides encoding each of TCR subunits, wherein the TCR formed by said subunits can bind to a complex of the peptide of any one of [1] to [5] and an HLA antigen on a cell surface;

[12] An isolated APC that presents on its surface a complex of an HLA antigen and the peptide of any one of [1] to [5];

[13] The APC of [12], which is induced by the method of [10];

[14] An isolated CTL that targets the peptide of any one of [1] to [5];

[15] The CTL of [14], which is induced by the method of [11];

[16] A method of inducing an immune response against cancer in a subject, wherein the method comprises the step of administering to the subject a composition comprising the peptide of any one of [1] to [5], or a polynucleotide encoding the peptide;

[17] An antibody or immunologically active fragment thereof against the peptide of any one of [1] to [5];

[18] A vector comprising a nucleotide sequence encoding the peptide of any one of [1] to [5];

[19] A host cell transformed or transfected with a vector of [18];

[20] A diagnostic kit comprising the peptide of any one of [1] to [5], the polynucleotide of [6] or the antibody or immunologically active fragment of [17]; and

[21] A method of screening for a peptide having an ability to induce a CTL that has specific cytotoxic activity against a cell that presents a fragment derived from KNTC2, wherein the method comprises the steps of:

(i) providing a candidate sequence consisting of an amino acid sequence modified by substituting, deleting, inserting and/or adding one, two or several amino acid residues to an original amino acid sequence, wherein the original amino acid sequence is selected from the group consisting of SEQ ID NOs: 2, 3, 7, 17, 41, 53 and 68;

(ii) selecting a candidate sequence that does not have substantial significant homology (or sequence identity) with the peptides derived from any known human gene products other than KNTC2;

(iii) contacting a peptide consisting of the candidate sequence selected in step (ii) with an antigen presenting cell;

(iv) contacting the antigen presenting cell of step (iii) with a CD8 positive T cell; and (v) identifying the peptide of which CTL inducibility is same to or higher than a peptide consisting of the original amino acid sequence.

[22] A pharmaceutical composition comprising a peptide of any one of [1] to [5];

[23] A peptide of any one of [1] to [5] for use as a medicament; and

[24] A polynucleotide of [6] or a vector of [18] for use as a medicament.

Alternatively, the present application also provides following embodiments:

[1] An isolated peptide having cytotoxic T lymphocyte (CTL) inducibility, wherein the CTL induced by the peptide have specific cytotoxic activity against a cell that presents a fragment derived from KNTC2, further wherein the peptide has an amino acid sequence (a) or (b) below:

(a) an amino acid sequence of an immunologically active fragment of KNTC2;

(b) an amino acid sequence in which 1, 2, or several amino acid(s) are substituted, deleted, inserted and/or added in an amino acid sequence of an immunologically active fragment of KNTC2;

[2] The peptide of [1], wherein the peptide has an amino acid sequence (a) or (b) below:

(a) an amino acid sequence selected from among SEQ ID NOs: 2, 3, 7, 17, 41, 53 and 68;

(b) an amino acid sequence in which 1, 2, or several amino acid(s) are substituted, deleted, inserted and/or added to an amino acid sequence selected from among SEQ ID NOs: 2, 3, 7, 17, 41, 53 and 68;

[3] The peptide of [2], wherein the peptide has one or both of the following characteristics:

(a) the second amino acid from the N-terminus is leucine or methionine; and (b) the C-terminal amino acid is valine or leucine;

[4] The peptide of any one of [1] to [3], wherein the peptide is a nonapeptide or a decapeptide;

[5] An isolated polynucleotide encoding the peptide of any one of [1] to [4];

[6] A composition for inducing a CTL, wherein the composition includes at least one active ingredient selected from among:

(a) the peptide of any one of [1] to [4];
(b) the polynucleotide of [5];

(c) an antigen-presenting cell (APC) that presents the peptide of any one of [1] to [4] on its surface; and (d) an exosome that presents the peptide of any one of [1] to [4] on its surface;

[7] A pharmaceutical composition for the treatment and/or prophylaxis of a primary cancer, and/or the prevention of a metastatic or post-operative recurrence thereof, or the induction of an immune response against said cancers, wherein the composition includes at least one active ingredient selected from among:

(a) the peptide of any one of [1] to [4];

(b) the polynucleotide of [5];

(c) an APC that presents the peptide of any one of [1] to [4] on its surface;

(d) an exosome that presents the peptide of any one of [1] to [4] on its surface; and (e) a CTL that can recognize a cell presenting the peptide of any one of [1] to [4];

[8] The pharmaceutical composition of [7], wherein the pharmaceutical composition is formulated for the administration to a subject whose HLA antigen is HLA-A2;

[9] A method for inducing an APC with CTL inducibility, wherein the method includes the step selected from among:

(a) contacting an APC with the peptide of any one of [1] to [4], and (b) introducing a polynucleotide encoding the peptide of any one of [1] to [4] into an APC;

[10] A method for inducing a CTL, wherein the method includes a step selected from among:

(a) co-culturing a CD8 positive T cell with an APC that presents on its surface a complex of an HLA antigen and the peptide of any one of [1] to [4];

(b) co-culturing a CD8 positive T cell with an exosome that presents on its surface a complex of an HLA antigen and the peptide of any one of [1] to [4]; and (c) introducing into a CD8 positive T cell a polynucleotide encoding both of T cell receptor (TCR) subunits or polynucleotides encoding each of TCR subunits, wherein the TCR formed by said subunits can bind to a complex of the peptide of any one of [1] to [4] and an HLA antigen on a cell surface;

[11] An isolated APC that presents on its surface a complex of an HLA antigen and the peptide of any one of [1] to [4];

[12] An APC of [11] induced by the method of [9];

[13] An isolated CTL that targets the peptide of any one of [1] to [4];

[14] A CTL of [13] induced by the method of [10];

[15] A method of inducing an immune response against cancer in a subject, wherein the method includes the step of administering to the subject a composition including the peptide of any one of [1] to [4], or a polynucleotide encoding the peptide;

[16] An antibody or immunologically active fragment thereof against the peptide of any one of [1] to [4];

[17] A vector containing a nucleotide sequence encoding the peptide of any one of [1] to [4];

[18] A host cell transformed or transfected with a vector of [17];

[19] A diagnostic kit that includes the peptide of any one of [1] to [4], the polynucleotide of [5] or the antibody or immunologically active fragment of [16]; and

[20] A method of screening for a peptide having an ability to induce a CTL that has specific cytotoxic activity against a cell that presents a fragment derived from KNTC2, wherein the method includes the steps of:

(i) providing a candidate sequence having an amino acid sequence modified by substituting, deleting, inserting and/or adding one, two or several amino acid residues to an original amino acid sequence, wherein the original amino acid sequence is selected from among SEQ ID NOs: 2, 3, 7, 17, 41, 53 and 68;

(ii) selecting a candidate sequence that does not have substantial significant homology with the peptides derived from any known human gene products other than KNTC2;

(iii) contacting a peptide having the candidate sequence selected in step (ii) with an antigen presenting cell;

(iv) contacting the antigen presenting cell of step (iii) with a CD8 positive T cell; and (v) identifying the peptide of which CTL inducibility is same to or higher than a peptide having the original amino acid sequence.

[21] A pharmaceutical composition including a peptide of any one of [1] to [4];

[22] A peptide of any one of [1] to [4] for use as a medicament; and

[23] A polynucleotide of [5] or a vector of [17] for use as a medicament.

Objects and features of the invention will become more fully apparent when the following detailed description is read in conjunction with the accompanying figures and examples. It is to be understood that both the foregoing summary of the present invention and the following detailed description are of exemplified embodiments, and not restrictive of the present invention or other alternate embodiments of the present invention.

In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments that follows.

DESCRIPTION OF EMBODIMENTS

Figure 1:
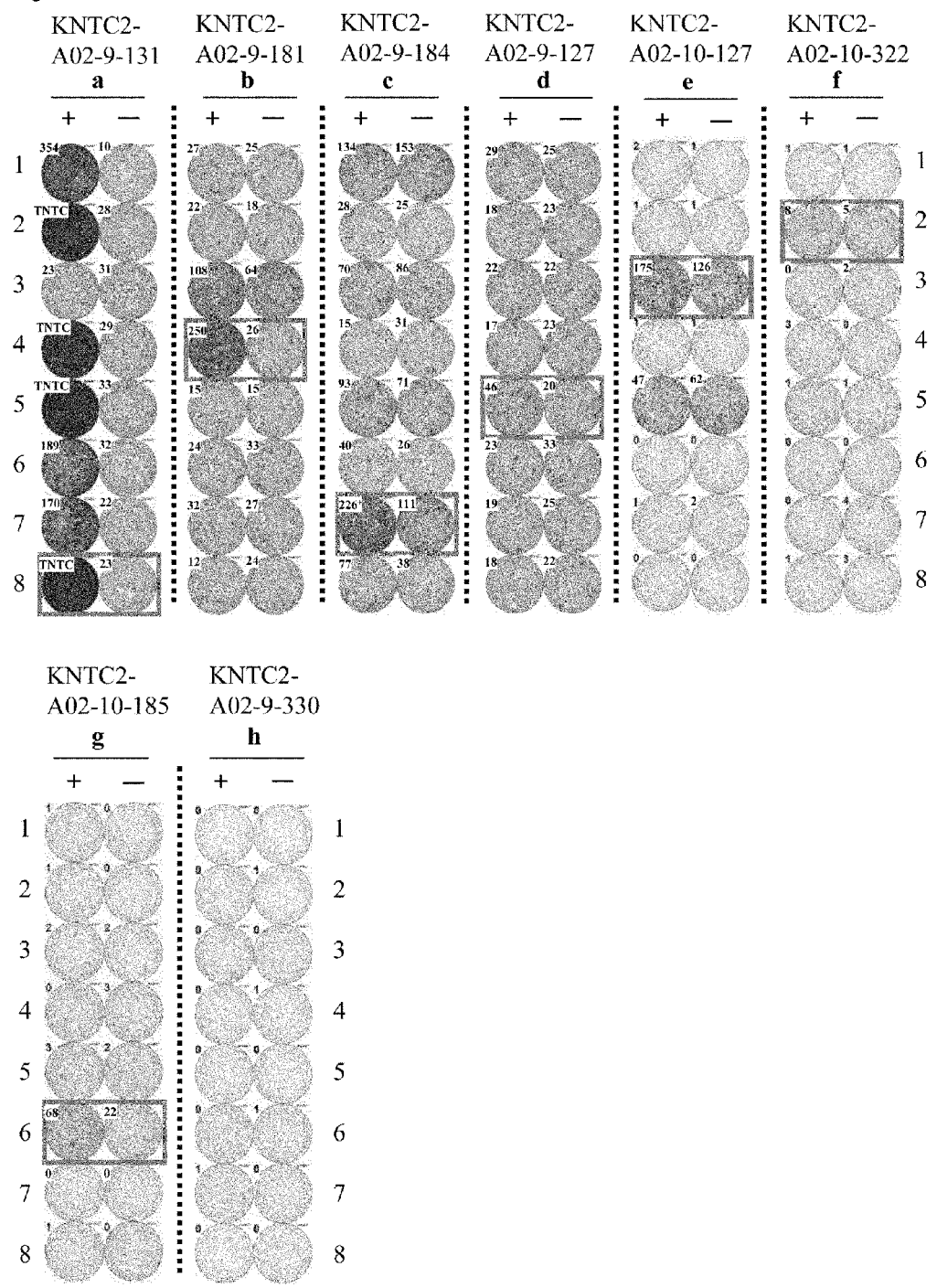
FIG. 1 is composed of a series of photographs, (a) to (h), depicting the results of interferon (IFN)-gamma enzyme-linked immunospot (ELISPOT) assay on CTLs that were induced with peptides derived from KNTC2. The CTLs in the well number #8 induced with KNTC2-A02-9-131 (SEQ ID NO: 2) (a), in #4 with KNTC2-A02-9-181 (SEQ ID NO: 3) (b), in #7 with KNTC2-A02-9-184 (SEQ ID NO: 7) (c), in #5 with KNTC2-A02-9-127 (SEQ ID NO: 17) (d), in #3 with KNTC2-A02-10-127 (SEQ ID NO: 41) (e), in #2 with KNTC2-A02-10-322 (SEQ ID NO: 53) (f) and in #6 with KNTC2-A02-10-185 (SEQ ID NO: 68) (g) showed potent IFN-gamma production as compared with the control, respectively. The square on the well of these pictures indicates that the cells from corresponding well were expanded to establish CTL lines. In contrast, as is typical of negative data, no specific IFN-gamma production was observed from the CTL stimulated with KNTC2-A02-9-330 (SEQ ID NO: 1) (h). In the figures, "+" indicates the IFN-gamma production against target cells pulsed with the appropriate peptide, and "−" indicates the IFN-gamma production against target cells not pulsed with any peptides.

Although any methods and materials similar or equivalent to those described herein can be used in the practice or testing of embodiments of the present invention, the preferred methods, devices, and materials are now described. However, before the present materials and methods are described, it should be understood that these descriptions are merely illustrative and not intended to be limited. It should also be understood that the present invention is not limited to the particular sizes, shapes, dimensions, materials, methodologies, protocols, etc. described herein, as these may vary in accordance with routine experimentation and optimization. Furthermore, the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

I. Definitions

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to a peptide that are substantially free of cellular material such as carbohydrate, lipid, or other contaminating proteins from the cell or tissue source from which the peptide is derived, or substantially free of chemical precursors or other chemicals when chemically synthesized. The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "oligopeptide" as used herein refers to a peptide which is composed of 20 amino acid residues or fewer, typically 15 amino acid residues or fewer. As used herein, the term "nonapeptide" refers to a peptide which is composed of 9 amino acid residues and the term "decapeptide" refers to a peptide which is composed of 10 amino acid resides.

The term "amino acid" as used herein refers to naturally occurring and synthetic amino acids, as well as amino acid analogs and amino acid mimetics that similarly function to the naturally occurring amino acids. Amino acids may be either L-amino acids ore D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbone (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "polynucleotide", "oligonucleotide", and "nucleic acid" are used interchangeably herein and, unless otherwise specifically indicated, are referred to by their commonly accepted single-letter codes.

The terms "agent" and "composition" are used interchangeably herein to refer to a product that includes specified ingredients in specified amounts, as well as any product that results, directly or indirectly, from combination of the specified ingredients in the specified amounts. Such terms, when used in relation to the modifier "pharmaceutical" (as in "pharmaceutical agent" and "pharmaceutical composition") are intended to encompass a product that includes the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the terms "pharmaceutical agent" and "pharmaceutical composition" refer to any product made by admixing a molecule or compound of the present invention and a pharmaceutically or physiologically acceptable carrier.

The term "active ingredient" herein refers to a substance in an agent or a composition that is biologically or physiologically active. Particularly, in the context of pharmaceutical agent or composition, the term "active ingredient" refers to a component substance that shows an objective pharmacological effect. For example, in case of pharmaceutical agents or compositions for use in the treatment or prevention of cancer, active ingredients in the agents or compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effects of active ingredients are inductions of CTLs that can recognize or kill cancer cells. Before being formulated, the "active ingredient" may also be referred to as "bulk", "drug substance" or "technical product".

The phrase "pharmaceutically acceptable carrier" or "physiologically acceptable carrier", as used herein, means a pharmaceutically or physiologically acceptable material, composition, substance or vehicle, including, but are not limited to, a liquid or solid filler, diluent, excipient, solvent and encapsulating material.

In some embodiments, pharmaceutical agents or compositions of the present invention find particular use as vaccines. In the context of the present invention, the term "vaccine" (also referred to as an "immunogenic composition") refers to an agent or a composition that has the function to improve, enhance and/or induce anti-tumor immunity upon inoculation into animals.

Unless otherwise defined, the term "cancer" refers to cancers or tumors that overexpress the KNTC2 gene, examples of which include, but are not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the term "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "subject's (or patient's) HLA antigen is HLA-A2" refers to that the subject or patient homozygously or heterozygously possess HLA-A2 antigen gene, and HLA-A2 antigen is expressed in cells of the subject or patient as an HLA antigen.

To the extent that the methods and compositions of the present invention find utility in the context of the "treatment" of cancer, a treatment is deemed "efficacious" if it leads to clinical benefit such as decrease in size, prevalence, or metastatic potential of cancer in a subject, prolongation of survival time, suppression of metastatic or post-operative recurrence and so on. When the treatment is applied prophylactically, "efficacious" means that it retards or prevents cancer from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of metastatic or post-operative recurrence thereof include any activity that leads to the following events, such as the surgical removal of cancer cells, the inhibition of the growth of cancerous cells, the involution or regression of a tumor, the induction of remission and suppression of occurrence of cancer, the tumor regression, and the reduction or inhibition of metastasis, the suppression of post operative recurrence of cancer, and prolongation of survival time. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity. An "antibody" indicates all classes (e.g., IgA, IgD, IgE, IgG and IgM).

Unless otherwise defined, all technical and scientific terms used herein have the same meaning as commonly understood by one of ordinary skill in the art to which this invention belongs.

II. Peptides

Peptides of the present invention described in detail below may be referred to as "KNTC2 peptide(s)" or "KNTC2 polypeptide(s)".

To demonstrate that peptides derived from KNTC2 function as an antigen recognized by CTLs, peptides derived from KNTC2 (SEQ ID NO: 79) were analyzed to determine whether they were antigen epitopes restricted by HLA-A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A2 binding peptides derived from KNTC2 were identified based on their binding affinities to HLA-A2. The following peptides were identified: SEQ ID NOs: 2 to 76.

Of the above, the following peptides resulted in the successful establishment of CTLs, after in vitro stimulation of T-cells by dendritic cells (DCs) pulsed (loaded) with these peptides, CTLs were successfully established using each of the following peptides:

KNTC2-HLA-A02-9-131 (SEQ ID NO: 2), KNTC2-HLA-A02-9-181 (SEQ ID NO: 3), KNTC2-HLA-A02-9-184 (SEQ ID NO: 7), KNTC2-HLA-A02-9-127 (SEQ ID NO: 17), KNTC2-HLA-A02-10-127 (SEQ ID NO: 41), KNTC2-HLA-A02-10-322 (SEQ ID NO: 53) and KNTC2-HLA-A02-10-185 (SEQ ID NO: 68).

The established CTLs noted above showed potent specific CTL activity against target cells pulsed with respective peptides. These results demonstrate that KNTC2 is an antigen recognized by CTLs and that the above peptides are epitope peptides of KNTC2 restricted by HLA-A2; therefore, such peptides may be effective in cancer immunotherapy through the induction of cytotoxicity by CTLs for HLA-A2 positive patients.

Since the KNTC2 gene is over-expressed in cancer cells and tissues, including for example those of bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor, and not expressed in most normal organs, it represents a good target for immunotherapy. Thus, the present invention provides nonapeptides (peptides composed of nine amino acid residues) and decapeptides (peptides composed of ten amino acid residues) corresponding to CTL-recognized epitopes from KNTC2. Alternatively, the present invention provides isolated peptides that can induce CTLs, wherein the peptide is composed of an immunologically active fragment of KNTC2. In some embodiments, the present invention provides peptides having an amino acid sequence selected from among SEQ ID NOs: 2, 3, 7, 17, 41, 53 and 68. In preferred embodiments, the peptides of the present invention are nonapeptides or decapeptides including an amino acid sequence selected from among SEQ ID NOs: 2, 3, 7, 17, 41, 53 and 68. The preferred examples of the peptides of the present invention includes peptides consisting of an amino acid sequence selected from among SEQ ID NOs: 2, 3, 7, 17, 41, 53 and 68.

The peptides of the present invention, particularly the nonapeptides and decapeptides of the present invention, may be flanked with additional amino acid residues, so long as the resulting peptide retains its CTL inducibility. The particular additional amino acid residues may be composed of any kind of amino acids, so long as they do not impair the CTL inducibility of the original peptide. Thus, the present invention encompasses peptides having CTL inducibility, in particular peptides derived from KNTC2. Such peptides are, for example, less than about 40 amino acids, often less than about 20 amino acids, and usually less than about 15 amino acids.

It is generally known that the modification of one, two or several amino acids in a peptide do not influence the function of the peptide, and in some cases even enhance the desired function of the original peptide. In fact, modified peptides (i.e., peptides composed of an amino acid sequence in which 1, 2 or several amino acid residues have been modified (i.e., substituted, added, deleted and/or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention have both CTL inducibility and an amino acid sequence selected from among SEQ ID NOs: 2, 3, 7, 17, 41, 53 and 68, in which one, two or even more amino acids are added and/or substituted. In other words, the peptides of the present invention have both CTL inducibility and an amino acid sequence in which one, two or several amino acid(s) are substituted, deleted, inserted and/or added in the amino acid sequence selected from among SEQ ID NOs: 2, 3, 7, 17, 41, 53 and 68, provided the modified peptides retain the CTL inducibility of the original reference peptide.

Those of skill in the art will recognize that individual modifications (i.e., deletions, insertions, additions and/or substitutions) to an amino acid sequence that alter a single amino acid or a small percentage of the overall amino acid sequence tend to result in the conservation of the properties of the original amino acid side-chain. As such, they are conventionally referred to as "conservative substitutions" or "conservative modifications", wherein the alteration of a protein results in a protein with similar functions to the original protein. Conservative substitution tables providing functionally similar amino acids are well known in the art. Examples of amino acid side-chains characteristics that are desirable to conserve include, for example: hydrophobic amino acids (A, I, L, M, F, P, W, Y, V), hydrophilic amino acids (R, D, N, C, E, Q, G, H, K, S, T), and side-chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and may include non-conservative modifications, so long as the resulting modified peptide retains the requisite CTL inducibility of the original unmodified peptide. Furthermore, the modified peptides should not exclude CTL inducible peptides derived from polymorphic variants, interspecies homologues, and alleles of KNTC2.

Amino acid residues may be inserted, substituted and/or added to the peptides of the present invention or, alternatively, amino acid residues may be deleted therefrom to achieve a higher binding affinity. To retain the requisite CTL inducibility, one of skill in the art preferably modifies (i.e., deletes, inserts, adds and/or substitutes) only a small number (for example, 1, 2 or several) or a small percentage of amino acids. Herein, the term "several" means 5 or fewer amino acids, for example, 4 or 3 or fewer. The percentage of amino acids to be modified may be, for example, 30% or less, preferably 20% or less, more preferably 15% of less, and even more preferably 10% or less, for example 1 to 5%.

When used in the context of cancer immunotherapy, the peptides of the present invention may be presented on the surface of a cell or exosome as a complex with an HLA antigen. Therefore, it is preferable to select peptides that not only induce CTLs but also possess high binding affinity to the HLA antigen. To that end, the peptides can be modified by substitution, insertion, deletion and/or addition of the amino acid residues to yield a modified peptide having improved binding affinity to the HLA antigen. In addition to peptides that are naturally displayed, since the regularity of the sequences of peptides displayed by binding to HLA antigens has already been known (Kubo R T et al., J Immunol 1994, 152: 3913-24; Rammensee H G et al., Immunogenetics 1995, 41: 178-228; Kondo et al., J Immunol 1994, 155: 4307-12; Falk K, et al., Nature. 1991 May 23; 351(6324):290-6), modifications based on such regularity may be introduced into the immunogenic peptides of the present invention.

For example, peptides possessing high HLA-A2 binding affinity tend to have the second amino acid from the N-terminus substituted with leucine or methionine and/or the amino acid at the C-terminus substituted with valine or leucine. Accordingly, it may be desirable to substitute the second amino acid from the N-terminus with leucine or methionine, and/or the amino acid at the C-terminus with valine or leucine in order to increase the HLA-A2 binding affinity. Thus, peptides having an amino acid sequence selected from among SEQ ID NOs: 2, 3, 7, 17, 41, 53 and 68, in which the second amino acid from the N-terminus of the amino acid sequence of the SEQ ID NO is substituted with leucine or methionine, and/or wherein the C-terminus of the amino acid sequence of the SEQ ID NO is substituted with valine or leucine are encompassed by the present invention. Also, the present invention encompasses the peptides including an amino acid sequence in which one, two or several amino acid are substituted, deleted, inserted and/or added in the amino acid sequence selected from among the SEQ ID NOs: 2, 3, 7, 17, 41, 53 and 68, such peptides having one or both of the following characteristic of (a) the second amino acid from the N-terminus is leucine or methionine; and (b) the C-terminal amino acid is valine or leucine. In preferred embodiments, the peptides of the present invention include an amino acid sequence in which the second amino acid from the N-terminus is substituted with leucine or methionine, and/or the C-terminal amino acid is substituted with valine or leucine in the amino acid sequence selected from among SEQ ID NOs: 2, 3, 7, 17, 41, 53 and 68.

Substitutions can be introduced not only at the terminal amino acids but also at the positions of potential T cell receptor (TCR) recognition sites of peptides. Several studies have demonstrated that a peptide with amino acid substitutions may have equal to or better function than that of the original, for example, CAP1, p53$_{(264-272)}$, Her-2/neu$_{(369-377)}$ or gp100$_{(209-217)}$ (Zaremba et al. Cancer Res. 57, 4570-4577, 1997, T. K. Hoffmann et al. J Immunol. (2002); 168(3): 1338-47, S. O. Dionne et al. Cancer Immunol immunother. (2003) 52: 199-206 and S. O. Dionne et al. Cancer Immunology, Immunotherapy (2004) 53, 307-314).

The present invention also contemplates the addition of 1, 2 or several amino acids can also be added to the N and/or C-terminus of the peptides of the present invention. Such modified peptides retaining CTL inducibility are also included in the present invention.

For example, the present invention provides an isolated peptide of less than 15, 14, 13, 12, 11, or 10 amino acids in length, which has CTL inducibility and an amino acid sequence selected from the group consisting of:
(i) an amino acid sequence in which 1, 2 or several amino acid(s) are modified in the amino acid sequence selected from the group consisting of SEQ ID NOs: 2, 3, 7, and 17,
(ii) the amino acid sequence of (i), wherein the amino acid sequence has one or both of the following characteristics:
(a) the second amino acid from the N-terminus of said SEQ ID NO is or is modified to be an amino acid selected from the group consisting of leucine and methionine; and
(b) the C-terminal amino acid of said SEQ ID NO is or is modified to be an amino acid selected from the group consisting of valine and leucine.

Moreover, the present invention also provides an isolated peptide of less than 15, 14, 13, 12, or 11 amino acids in length, which has CTL inducibility and an amino acid sequence selected from the group consisting of:
(i') an amino acid sequence in which 1, 2 or several amino acid(s) are modified in the amino acid sequence selected from the group consisting of SEQ ID NOs: 41, 53 and 68,
(ii') the amino acid sequence of (i'), wherein the amino acid sequence has one or both of the following characteristics:
(a) the second amino acid from the N-terminus of said SEQ ID NOs is or is modified to be an amino acid selected from the group consisting of leucine and methionine; and
(b) the C-terminal amino acid of said SEQ ID NOs is or is modified to be an amino acid selected from the group consisting of valine and leucine.

These peptides are processed in an APC to present a peptide selected from the group consisting of (i) to (ii) and (i') to (ii') thereon, when these peptides are contacted with, or introduced in APC.

However, when the peptide sequence is identical to a portion of the amino acid sequence of an endogenous or exogenous protein having a different function, negative side effects such as autoimmune disorders and/or allergic symptoms against specific substances may be induced. Therefore, it may be desirable to first perform homology searches using available databases to avoid situations in which the sequence of the peptide matches the amino acid sequence of another protein. When it becomes clear from the homology searches that no peptide identical to or having only 1 or 2 amino acid differences as compared to the objective peptide exists in nature, the objective peptide can be modified in order to increase its binding affinity with HLA antigens, and/or increase its CTL inducibility without any danger of such side effects.

Although peptides having high binding affinity to the HLA antigens are expected to be highly effective, the candidate peptides, which are selected according to the presence of high binding affinity as an indicator, are further examined for the presence of CTL inducibility. Herein, the phrase "CTL inducibility" indicates the ability of a peptide to induce a cytotoxic T lymphocyte (CTL) when presented on an antigen-presenting cell (APC). Further, "CTL inducibility" includes the ability of a peptide to induce CTL activation, CTL proliferation, promote lysis of target cells by a CTL, and to increase IFN-gamma production by a CTL.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation of APCs with a test peptides, mixing the APCs with CD8 positive T cells to induce CTLs, and then measuring the IFN-gamma against the target cells produced and released by CTLs. As the reaction system, transgenic animals that have been produced to express a human HLA antigen (for example, those described in BenMohamed L, et al., Hum Immunol 2000, 61(8): 764-79, Related Articles, Books, Linkout Induction of CTL response by a minimal epitope vaccine in HLA-A*0201/DR1 transgenic mice: dependence on HLA class II restricted T(H) response) can be used. Alternatively, the target cells may be radiolabeled with $^{51}$Cr and such, and cytotoxic activity of CTLs may be calculated from radioactivity released from the target cells. Alternatively, CTL inducibility can be assessed by measuring IFN-gamma produced and released by CTLs in the presence of cells that carry immobilized peptides, and visualizing the inhibition zone on the media using anti-IFN-gamma monoclonal antibodies.

In addition to the above-described modifications, the peptides of the present invention can also be linked to other peptides, so long as the resulting linked peptide retains the requisite CTL inducibility of the original peptide, and more preferably also retains the requisite HLA binding activity thereof. Examples of suitable "other" peptides include: the peptides of the present invention or the CTL-inducible peptides derived from other TAAs. The peptide of the present invention can be linked to one or more "other" peptides either directly or indirectly via a linker. The linkers between the peptides are well known in the art and include, for example AAY (P. M. Daftarian et al., J Trans Med 2007, 5:26), AAA, NKRK (SEQ ID NO: 84) (R. P. M. Sutmuller et al., J Immunol. 2000, 165: 7308-7315) or K (S. Ota et al., Can Res. 62, 1471-1476, K. S. Kawamura et al., J Immunol. 2002, 168: 5709-5715).

The above described linked peptides are referred to herein as "polytopes", i.e., groups of two or more potentially immunogenic or immune response stimulating peptides which can be joined together in various arrangements (e.g., concatenated, overlapping). The polytope (or nucleic acid encoding the polytope) can be administered in accordance with a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci USA 92(13):5845-5849, 1995; Gilbert et al., Nature Biotechnol. 15(12):1280-1284, 1997; Thomson et al., J Immunol. 157(2):822-826, 1996; Tarn et al., J Exp. Med. 171(1):299-306, 1990). Polytopes containing various numbers and combinations of epitopes can be prepared and tested for recognition by CTLs and for efficacy in increasing an immune response.

The peptides of the present invention may also be linked to other substances, so long as the resulting linked peptide retains the requisite CTL inducibility of the original peptide. Examples of suitable substances include, for example: peptides, lipids, sugar and sugar chains, acetyl groups, natural and synthetic polymers, etc. The peptides may contain modifications such as glycosylation, side chain oxidation, or phosphorylation, etc., provided the modifications do not destroy the biological activity of the original peptide. These kinds of modifications may be performed to confer additional functions (e.g., targeting function, and delivery function) or to stabilize the peptide.

For example, to increase the in vivo stability of a peptide, it is known in the art to introduce D-amino acids, amino acid mimetics or unnatural amino acids; this concept can also be adapted to the peptides of the present invention. The stability of a peptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides in which are substituted, deleted inserted and/or added by 1, 2 or several amino acid residues, those having same or higher activity as compared to original peptides can be screened for or selected. The present invention, therefore, also provides the method of screening for or selecting modified peptides having same or higher activity as compared to originals. An illustrative method includes the steps of:

a: modifying (i.e., substituting, deleting, inserting and/or adding) at least one amino acid residue of a peptide of the present invention, b: determining the activity of the peptide modified in step a, and c: selecting the peptide having same or higher activity as compared to the original peptide.

Herein, the activity to be assayed may include MHC binding activity, APC or CTL inducibility and cytotoxic activity. Preferably, the activity of the peptide to be assayed is CTL inducibility.

In preferred embodiments, the present invention provides a method of screening for a peptide having an ability to induce a CTL that has specific cytotoxic activity against a cell that presents a fragment derived from KNTC2, wherein the method includes the steps of:

(i) providing a candidate sequence consisting of an amino acid sequence modified by substituting, deleting, inserting and/or adding one, two or several amino acid residues to an original amino acid sequence, wherein the original amino acid sequence is selected from the group consisting of SEQ ID NOs: 2, 3, 7, 17, 41, 53 and 68;

(ii) selecting a candidate sequence that does not have substantial significant homology (or sequence identity) with the peptides derived from any known human gene products other than KNTC2;

(iii) contacting a peptide consisting of the candidate sequence selected in step (ii) with an antigen presenting cell;

(iv) contacting the antigen presenting cell of step (iii) with a CD8 positive T cell; and (v) identifying the peptide of which CTL inducibility is same to or higher than a peptide consisting of the original amino acid sequence.

When the peptides of the present invention include a cysteine residue (e.g., SEQ ID NO: 7), the peptides tend to form dimers via a disulfide bond between SH groups of the cysteine residues. Therefore, the present invention extends to peptide dimers having the ability to induce CTL. A peptide dimmer of the present invention may be formed by binding two KNTC2 peptide monomers through a disulfide bond between cysteine residues present in or added to the monomers. When an amino acid sequence of each peptide contains a cysteine residue (Cys), a disulfide bond may be formed between such cysteine residues to form the oligomeric peptide of the present invention. Alternatively, if an amino acid sequence itself has no cysteine, a disulfide bond may be formed between cysteine residues that are added into such amino acid sequence. For example, a cysteine residue(s) may be introduced into each peptide at either or both of C- and N-termini thereof to form a disulfide bond. Moreover, one or more cysteine residues may also be inserted within the amino acid sequence of each peptide.

III. Preparation of KNTC2 Peptides

The peptides of the present invention can be prepared using well known techniques. For example, the peptides can be prepared synthetically, using recombinant DNA technology or chemical synthesis. The peptides of the present invention can be synthesized individually or as longer polypeptides including two or more peptides. The peptides can then be isolated i.e., purified or isolated so as to be substantially free of other naturally occurring host cell proteins and fragments thereof, or any other chemical substances.

The peptides of the present invention may contain modifications, such as glycosylation, side chain oxidation, or phosphorylation, provided the modifications do not destroy the biological activity of the original peptide. Other illustrative modifications include incorporation of one or more D-amino acids or other amino acid mimetics that can be used, for example, to increase the serum half life of the peptides.

Peptides of the present invention can be obtained through chemical synthesis based on the selected amino acid sequence. For example, conventional peptide synthesis methods that can be adopted for the synthesis include:
  (i) Peptide Synthesis, Interscience, New York, 1966;
  (ii) The Proteins, Vol. 2, Academic Press, New York, 1976;
  (iii) Peptide Synthesis (in Japanese), Maruzen Co., 1975;
  (iv) Basics and Experiment of Peptide Synthesis (in Japanese), Maruzen Co., 1985;
  (v) Development of Pharmaceuticals (second volume) (in Japanese), Vol. 14 (peptide synthesis), Hirokawa, 1991;
  (vi) WO99/67288; and
  (vii) Barany G. & Merrifield R. B., Peptides Vol. 2, "Solid Phase Peptide Synthesis", Academic Press, New York, 1980, 100-118.

Alternatively, the peptides of the present invention can be obtained adopting any known genetic engineering method for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. Such vectors and host cells are also provided by the present invention. The host cell is then cultured to produce the peptide of interest. The peptide can also be produced in vitro adopting an in vitro translation system.

When the peptides of the present invention are peptide dimers, such dimers can be prepared using a method known in the art. For example, if the peptide monomers include one pair of cysteine residues, the peptide dimer can be prepared, for example, by removing all the protecting groups including the ones on the cysteine side chains, and then subjecting the resulting monomer solution to air-oxidation under alkaline conditions, or adding an oxidant under alkaline or acidic conditions to form a disulfide bond. Examples of the oxidants include iodine, dimethyl sulfoxide (DMSO) and potassium ferricyanide.

The peptide monomers including two or more cysteine residues can also be prepared by the method as described above. In this case, isomers having different types of disulfide bonds are obtained. On the other hand, a peptide dimer in which a disulfide bond is formed between particular cysteine residues can be prepared by selecting a combination of protecting groups for cysteine side chains. Examples of the combinations of the protecting groups include combinations of MeBzl (methylbenzyl) group and Acm (acetamidemethyl) group, Trt (trityl) group and Acm group, Npys (3-nitro-2-pyridylthio) group and Acm group, and S-Bu-t (S-tert-butyl) group and Acm group. For example, in the case of the combination of MeBzl group and Acm group, the peptide dimer preparation can be performed by removing the MeBzl group and the protecting group other than on the cysteine side chain, subjecting the resulting monomer solution to air-oxidation to form a disulfide bond between the de-protected cysteine residues, and then de-protecting and oxidizing using iodine to form a disulfide bond between the cysteine residues previously protected by Acm.

IV. Polynucleotides

The present invention also provides polynucleotides that encode any of the aforementioned peptides of the present invention. These include polynucleotides derived from the natural occurring KNTC2 gene (e.g., GenBank Accession No. NM_006101 (SEQ ID NO: 77) or AF017790 (SEQ ID NO: 78)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotides of the present invention can be composed of DNA, RNA, and derivatives thereof. As is well known in the art, a DNA is suitably composed of bases such as A, T, C, and G, and T is replaced by U in an RNA. One of skill in the art will recognize that non-naturally occurring bases may be included in polynucleotides, as well.

The polynucleotides of the present invention can encode multiple peptides of the present invention with or without intervening amino acid sequences. For example, the intervening amino acid sequence can provide a cleavage site (e.g., enzyme recognition sequence) of the polynucleotide or the translated peptides. Furthermore, a polynucleotide of the present invention can include any additional sequences to the coding sequence encoding a peptide of the present invention. For example, a polynucleotide of the present invention can be a recombinant polynucleotide that includes regulatory sequences required for the expression of the peptide or can be an expression vector (plasmid) with a marker gene and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, the polynucleotides of the present invention can be produced by insertion into an appropriate vector, which can be expressed when transfected into a competent cell. Alternatively, the polynucleotides of the present invention can be amplified using PCR techniques or expression in suitable hosts (see, e.g., Sambrook et al., Molecular Cloning: A Laboratory Manual, Cold Spring Harbor Laboratory, New York, 1989). Alternatively, the polynucleotide of the present invention can be synthesized using the solid phase techniques, as described in Beaucage S L & Iyer R P, Tetrahedron 1992, 48: 2223-311; Matthes et al., EMBO J 1984, 3: 801-5.

V. Exosomes

The present invention further provides intracellular vesicles called exosomes that present complexes formed between the peptides of the present invention and HLA antigens on their surface. Exosomes can be prepared, for example, using the methods detailed in Japanese Patent Publication No. H11-510507 and WO99/03499, and can be prepared using APCs obtained from patients who are subject to treatment and/or prevention. The exosomes of the present invention can be inoculated as vaccines, in a fashion similar to the peptides of the present invention.

The type of HLA antigens included in the complexes must match that of the subject requiring treatment and/or prevention. For example, in the Japanese population, HLA-A2, particularly HLA-A*0201 and HLA-A*0206, are prevalent and therefore would be appropriate for treatment of Japanese patients. The use of the HLA-A2 type that are frequently expressed among the Japanese and Caucasian population is favorable for obtaining effective results, and subtypes such as HLA-A*0201 and HLA-A*0206 also find use. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, insertion, deletion and/or addition of 1, 2, or several amino acids can be performed based on the amino acid sequence of the naturally occurring KNTC2 partial peptide.

When using the HLA-A2 type of HLA antigen for the exosome of the present invention, peptides having an amino acid sequence selected from among SEQ ID NOs: 2, 3, 7, 17, 41, 53 and 68 have particular utility.

In some embodiments, the exosomes of the present invention present a complex of a peptide of the present invention and an HLA-A2 antigen on their surface.

VI. Antigen-Presenting Cells (APCs)

The present invention also provides isolated antigen-presenting cells (APCs) that present complexes formed between HLA antigens and the peptides of the present invention on its surface. The APCs can be derived from patients who are subject to treatment and/or prevention, and can be administered as vaccines by themselves or in combination with other drugs including the peptides, exosomes, or CTLs of the present invention.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DCs are representative APCs having the strongest CTL inducing activity among APCs, DCs are suitable for the APCs of the present invention.

For example, the APCs of the present invention can be obtained by inducing DCs from peripheral blood monocytes and then contacting (stimulating) them with the peptides of the present invention in vitro, ex vivo or in vivo. When the peptides of the present invention are administered to a subject, APCs that present the peptides of the present invention are induced in the body of the subject. Therefore, the APCs of the present invention can be obtained by collecting the APCs from a subject after administering the peptides of the present invention to the subject. Alternatively, the APCs of the present invention can be obtained by contacting APCs collected from a subject with a peptide of the present invention.

The APCs of the present invention can be administered to a subject for inducing immune response against cancer in the subject by themselves or in combination with other drugs including the peptides, exosomes or CTLs of the present invention. For example, the ex vivo administration can include steps of:
  a: collecting APCs from a first subject,
  b: contacting the APCs of step a, with a peptide of the present invention, and
  c: administering the APCs of step b to a second subject.

The first subject and the second subject can be the same individual, or may be different individuals. The APCs obtained by step b can be formulated and administered as a vaccine for the treatment and/or prevention of cancer, such as bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor, but not limited thereto.

In the context of the present invention, one may utilize the peptides of the present invention for manufacturing a pharmaceutical composition capable of inducing an APC. The present invention also provides a method or process for manufacturing a pharmaceutical composition for inducing an APC, wherein the method includes the step of admixing or formulating the peptide of the invention with a pharmaceutically acceptable carrier.

The present invention also provides for the use of the peptides of the present invention for inducing APCs.

According to an aspect of the present invention, the APCs of the present invention have CTL inducibility. In the context of the APCs, the phrase "CTL inducibility" refers to the ability of an APC to induce a CTL when contacted with a CD8 positive T cell. Further, "CTL inducibility" includes the ability of an APC to induce CTL activation, CTL proliferation, promote lysis of a target cell by a CTL, and to increase IFN-gamma production by a CTL. In particular, the APCs of the present invention have an ability to induce CTLs specific to KNTC2. Such APCs having CTL inducibility can be prepared by a method that includes the step of transferring a polynucleotide encoding a peptide of the present invention to APCs in vitro as well as the method mentioned above. The introduced gene can be in the form of DNA or RNA. Examples of methods for introduction include, without particular limitations, various methods conventionally performed in this field, such as lipofection, electroporation, and calcium phosphate method can be used. More specifically, it can be performed as described in Reeves M E et al., Cancer Res 1996, 56: 5672-7; Butterfield L H et al., J Immunol 1998, 161: 5607-13; Boczkowski D et al., J Exp Med 1996, 184: 465-72; Japanese Patent Publication No. 2000-509281. By transferring the gene into APCs, the gene undergoes transcription, translation, and such in the cell, and then the obtained protein is processed by MHC Class I or Class II, and proceeds through a presentation pathway to present partial peptides. Alternatively, APCs of the present invention can be prepared by a method that includes the step of simply contacting APCs with a peptide of the present invention.

In some embodiments, the APCs of the present invention present complexes of HLA-A2 antigen and the peptide of the present invention on their surface.

VII. Cytotoxic T Lymphocytes (CTLs)

A CTL induced against any one of the peptides of the present invention strengthens the immune response targeting cancer cells in vivo and thus can be used as vaccines, in a fashion similar to the peptides per se. Thus, the present invention provides isolated CTLs that are specifically induced or activated by any one of the peptides of the present invention.

Such CTLs can be obtained by (1) administering the peptide(s) of the present invention to a subject, (2) contacting (stimulating) subject-derived APCs, and CD8 positive T cells, or peripheral blood mononuclear leukocytes in vitro with the peptide(s) of the present invention, (3) contacting CD8 positive T cells or peripheral blood mononuclear leukocytes in vitro with the APCs or exosomes presenting a complex of an HLA antigen and the peptide on its surface or (4) introducing into a CD8 positive T cell a polynucleotide encoding both of T cell receptor (TCR) subunits or polynucleotides encoding each of TCR subunits, wherein the TCR formed by such subunits can bind a complex of a peptide of the present invention and HLA antigen on a cell surface. Such APCs or exosomes can be prepared by the methods described above. Details of the method of (4) are described below in section "VIII. T Cell Receptor (TCR)".

The CTLs of the present invention can be derived from patients who are subject to treatment and/or prevention, and can be administered by themselves or in combination with other drugs including the peptides, APCs or exosomes of the present invention for the purpose of regulating effects. The obtained CTLs act specifically against target cells presenting the peptides of the present invention, for example, the same peptides used for induction. The target cells can be cells that endogenously express KNTC2, such as cancer cells, or cells that are transfected with the KNTC2 gene; and cells that present a peptide of the present invention on the cell surface due to stimulation by the peptide can also serve as targets of activated CTL attack.

In some embodiments, the CTLs of the present invention recognize cells presenting complexes of HLA-A2 antigen and a peptide of the present invention. In the context of the CTL, the phrase "recognize a cell" refers to binding a complex of HLA-A2 antigen and a peptide of the present invention on the cell surface via its TCR and showing specific cytotoxic activity against the cell. Herein, "specific cytotoxic activity" refers to showing cytotoxic activity against the cell presenting a complex of HLA-A2 antigen and a peptide of the present invention but not other cells. Accordingly, the CTLs that show specific cytotoxic activity against a cell presenting a peptide of the present invention are included in the present invention. Specifically, the CTLs of the present invention can recognize a cell expressing KNTC2 and an HLA-A2 (e.g., HLA-A2 positive cancer cell) and show specific cytotoxic activity against such cell.

VIII. T Cell Receptor (TCR)

The present invention also provides a composition that includes one or more polynucleotides encoding both of TCR subunits or polynucleotides encoding each of TCR subunits, wherein the TCR formed by such subunits can bind to a complex of an HLA antigen and the peptide of the present invention on a cell surface. Method of using the same are also contemplated. Such TCR subunits have the ability to form TCRs that confer specificity to T cells against tumor cells expressing KNTC2. By using the known methods in the art, the polynucleotides encoding each of alpha- and beta-chains of the TCR subunits of the CTL induced with one or more peptides of the present invention can be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccaggcattcgcttcat-3') as 5' side primers (SEQ ID NO: 80) and 3-TRa-C primers (5'-tcagctggaccacagccgcagcgt-3') specific to TCR alpha chain C region (SEQ ID NO: 81), 3-TRb-C1 primers (5'-tcagaaatcctttctcttgac-3') specific to TCR beta chain C1 region (SEQ ID NO: 82) or 3-TRb-C2 primers (5'-ctagc-ctctggaatcctttctctt-3') specific to TCR beta chain C2 region (SEQ ID NO: 83) as 3' side primers, but not limited thereto. The derivative TCRs can bind target cells presenting a peptide of the present invention with high avidity, and optionally mediate efficient killing of target cells presenting a peptide of the present invention in vivo and in vitro.

The polynucleotide encoding both of the TCR subunits or polynucleotides encoding each of the TCR subunits can be incorporated into suitable vectors, e.g., retroviral vectors. These vectors are well known in the art. The polynucleotides or the vectors including them usefully can be transferred into a T cell (e.g., CD8 positive T cell), for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

Specific TCRs against peptides of the present invention should be capable of specifically recognizing a complex of a peptide of the present invention and an HLA molecule, giving a T cell specific activity against a target cell presenting a complex of a peptide of the present invention and an HLA antigen when the TCR is presented on the surface of the T cell. A specific recognition of the above complex may be confirmed by any known methods, preferred examples of which include HLA multimer staining analysis using HLA molecules and peptides of the present invention, and ELISPOT assay. By performing the ELISPOT assay, it can be confirmed that a T cell expressing the TCR on the cell surface recognizes a cell by the TCR, and that signals are transmitted intracellularly. The confirmation that the above-mentioned TCR can give a T cell cytotoxic activity when the TCR exists on the T cell surface may also be carried out by a known method. A preferred method includes, for example, the determination of cytotoxic activity against an HLA positive target cell, such as chromium release assay.

Also, the present invention provides CTLs which are prepared by transduction with the polynucleotides encoding both of the TCR subunits or polynucleotides encoding each of the TCR subunits wherein the TCR formed by such TCR subunits can bind to the KNTC2 peptide, e.g., SEQ ID NOs: 2, 3, 7, 17, 41, 53 and 68 in the context of HLA-A2.

The transduced CTLs are capable of homing to cancer cells in vivo, and can be expanded by well known culturing methods in vitro (e.g., Kawakami et al., J Immunol., 142, 3452-3461 (1989)). The CTLs of the present invention can be used to form an immunogenic composition useful in either or both of the treatment and prevention of cancer in a patient in need of therapy or protection (See, WO2006/031221, the contents of which are incorporated by reference herein).

IX. Pharmaceutical Compositions

Since KNTC2 expression is specifically elevated in cancers, examples of which include, but are not necessarily limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor as compared to normal tissues, the peptides or polynucleotides of the present invention may be used to induce an immune response against a cancer or tumor cell and thus serve in the treatment and/or prophylaxis of cancer, and/or for the prevention of a metastatic- or post-operative recurrence thereof. Thus, the present invention provides pharmaceutical compositions or agents formulated for the treatment and/or prophylaxis of cancer, and/or for the prevention of a metastatic- or post-operative recurrence thereof, such compositions or agents including at least one of the peptides or polynucleotides of the present invention as an active ingredient. Alternatively, the peptides of the present invention can be expressed on the surface of any of the foregoing exosomes or cells, such as APCs for the use as pharmaceutical compositions or agents. In addition, the aforementioned CTLs which target any one of the peptides of the present invention can also be used as the active ingredient of the pharmaceutical compositions or agents of the present invention.

Accordingly, the present invention provides agents or compositions that include at least one active ingredient selected from among:
  (a) a peptide of the present invention;
  (b) a polynucleotide encoding a peptide of the present invention in an expressible form;
  (c) an APC of the present invention;
  (d) an or an exosome of the present invention; and
  (e) a CTL of the present invention.

In the pharmaceutical composition or agent, such peptide, polynucleotide, APC, and CTL are present in a therapeutically or pharmaceutically effective amount.

The pharmaceutical compositions or agents of the present invention also find use as a vaccine. In the context of the present invention, the phrase "vaccine" (also referred to as an "immunogenic composition") refers to an agent or a composition that has the function to improve, enhance and/or induce anti-tumor immunity upon inoculation into an animal. In other words, the present invention provides the pharmaceutical agents or compositions for inducing an immune response against cancer in a subject.

The pharmaceutical compositions or agents of the present invention can be used to treat and/or prevent cancers, and/or prevent a metastatic- or post-operative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal. In some embodiments, the pharmaceutical agents or compositions of the present invention can be formulated for the administration to a subject whose HLA antigen is HLA-A2.

In another embodiment, the present invention also provides the use of an active ingredient in manufacturing a pharmaceutical composition or agent for treating and/or preventing a cancerous or tumorous condition, and/or preventing a metastatic or post-operative recurrence thereof, said active ingredient selected from among:
  (a) a peptide of the present invention;
  (b) a polynucleotide encoding a peptide of the present invention in an expressible form;
  (c) an APC presenting a peptide of the present invention on its surface;
  (d) an exosome presenting a peptide of the present invention on its surface; and
  (e) a CTL of the present invention.

Alternatively, the present invention further provides an active ingredient for use in the treatment and/or prevention of cancers or tumors, and/or prevention of a post-operative recurrence thereof, said active ingredient selected from among:
  (a) a peptide of the present invention;
  (b) a polynucleotide encoding a peptide of the present invention in an expressible form;
  (c) an APC presenting a peptide of the present invention on its surface;
  (d) an exosome presenting a peptide of the present invention on its surface; and
  (e) a CTL of the present invention.

Alternatively, the present invention further provides a method or process for manufacturing a pharmaceutical composition or agent for treating and/or preventing a cancerous or tumorous condition, and/or preventing a metastatic or post-operative recurrence thereof, wherein the method or process includes the step of formulating a pharmaceutically or physiologically acceptable carrier with an active ingredient selected from among:
  (a) a peptide of the present invention;
  (b) a polynucleotide encoding a peptide of the present invention in an expressible form;
  (c) an APC presenting a peptide of the present invention on its surface;
  (d) an exosome presenting a peptide of the present invention on its surface; and
  (e) a CTL of the present invention.

In another embodiment, the present invention also provides a method or process for manufacturing a pharmaceutical composition or agent for treating and/or preventing a cancerous or tumorous condition, and/or preventing a metastatic or post-operative recurrence thereof, wherein the method or process includes the steps of admixing an active ingredient with a pharmaceutically or physiologically acceptable carrier, wherein the active ingredient is selected from among:
  (a) a peptide of the present invention;
  (b) a polynucleotide encoding a peptide of the present invention in an expressible form;
  (c) an APC presenting a peptide of the present invention on its surface;
  (d) an exosome presenting a peptide of the present invention on its surface; and
  (e) a CTL of the present invention.

In another embodiment, the present invention also provides a method for treating and/or preventing a cancerous or tumorous condition, and/or preventing a metastatic or post-operative recurrence thereof, wherein the method includes the step of administering to a subject at least one active ingredient selected from among:
  (a) a peptide of the present invention;
  (b) a polynucleotide encoding such a peptide of the present invention in an expressible form;

(c) an APC presenting a peptide of the present invention on its surface;

(d) an exosome presenting a peptide of the present invention on its surface; and (e) a CTL of the present invention.

According to the present invention, peptides having an amino acid sequence selected from among SEQ ID NOs: 2, 3, 7, 17, 41, 53 and 68 have been shown to be HLA-A2 restricted epitope peptides and thus serve as the candidates that can induce potent and specific immune response against cancer expressing HLA-A2 and KNTC2 in a subject. Therefore, the pharmaceutical compositions or agents including any of these peptides with the amino acid sequence selected from among SEQ ID NOs: 2, 3, 7, 17, 41, 53 and 68 are particularly suited for the administration to subjects whose HLA antigen is HLA-A2. The amount of the peptide in such agent or composition may be an amount that is effective in significantly inducing potent and specific immunological response in a subject carrying a cancer expressing KNTC2 and HLA-A2. The same applies to pharmaceutical compositions or agents that contain polynucleotides encoding any of these peptides (i.e., the polynucleotides of the present invention).

Cancers to be treated and/or prevented by the pharmaceutical compositions or agents of the present invention are not limited and include all kinds of cancers in which KNTC2 is involved, examples of which include, but not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor Preferably, cancer expresses HLA-A2 (i.e., HLA-A2 positive cancer).

The pharmaceutical compositions or agents of the present invention can contain in addition to the aforementioned active ingredients, other peptides that have the ability to induce CTLs against cancerous cells, polynucleotides encoding such peptides, cells that present such peptides, and the like. Examples of such "other" peptides having the ability to induce CTLs against cancerous cells include, but are not limited to, peptides derived from cancer specific antigens (e.g., identified TAAs).

If necessary, the pharmaceutical compositions or agents of the present invention can optionally include other therapeutic substances as additional active ingredients, so long as the substance does not inhibit the antitumoral effect of the active ingredient of the present invention, e.g., any of the peptides, polynucleotides, exosomes, APCs, CTLs of the present invention. For example, formulations can include anti-inflammatory substances, pain killers, chemotherapeutics, and the like. In addition to including other therapeutic substances in the medicament itself, the medicaments of the present invention can also be administered sequentially or concurrently with the one or more other pharmacologic compositions. The amounts of medicament and pharmacologic composition depend, for example, on what type of pharmacologic composition(s) is/are used, the disease being treated, and the scheduling and routes of administration.

Those of skill in the art will recognize that in addition to the ingredients particularly mentioned herein, the pharmaceutical compositions or agent of the present invention can include other substances conventional in the art having regard to the type of formulation in question.

In one embodiment of the present invention, the pharmaceutical compositions or agents of the present invention can be packaged in articles of manufacture and kits containing materials useful for treating the pathological conditions of the disease to be treated, e.g., cancer. The article of manufacture can include a container of any of the present pharmaceutical compositions or agents with a label. Suitable containers include bottles, vials, and test tubes. The containers can be formed from a variety of materials, such as glass or plastic. The label on the container should indicate the composition or agent is used for treating or prevention of one or more conditions of the disease. The label can also indicate directions for administration and so on.

In addition to the container described above, a kit that includes a pharmaceutical composition or agent of the present invention can optionally further include a second container housing a pharmaceutically-acceptable diluent. It can further include other materials desirable from a commercial or user standpoint, including other buffers, diluents, filters, needles, syringes, and package inserts with instructions for use.

The pharmaceutical compositions or agents of the present invention can, if desired, be packaged in a pack or dispenser device that can contain one or more unit dosage forms containing the active ingredient. The pack can, for example, include metal or plastic foil, such as a blister pack. The pack or dispenser device can be accompanied by instructions for administration.

(1) Pharmaceutical Compositions Containing the Peptides

The peptides of the present invention can be administered directly as pharmaceutical compositions or agents, or if necessary, may be formulated by conventional formulation methods. In the latter case, in addition to the peptides of the present invention, carriers, excipients, and such that are ordinarily used for drugs can be included as appropriate without particular limitations. Examples of such carriers include, but are not limited to, sterilized water, physiological saline, phosphate buffer, culture fluid and such. Furthermore, the pharmaceutical compositions or agents of the present invention can contain as necessary, stabilizers, suspensions, preservatives, surfactants and such. The pharmaceutical compositions or agents of the present invention can be used for anticancer purposes.

The peptides of the present invention can be prepared in combination, which includes two or more of peptides of the present invention, to induce CTLs in vivo. The peptides can be in a cocktail or can be conjugated to each other using standard techniques. For example, the peptides can be chemically linked or expressed as a single fusion polypeptide. The peptides in the combination can be the same or different. By administering the peptides of the present invention, the peptides are presented in high density by the HLA antigens on APCs, and then CTLs that specifically react toward the complex formed between the displayed peptide and the HLA antigen are induced. Alternatively, APCs (e.g., DCs) may be removed from a subject and then stimulated by the peptides of the present invention to obtain APCs that present any of the peptides of the present invention on their cell surface. These APCs can be re-administered to the subject to induce CTLs in the subject's body, and as a result, aggressiveness towards the tumor-associated endothelium can be increased.

The pharmaceutical compositions or agents for the treatment and/or prevention of cancer, that include any of peptides of the present invention as the active ingredient, can also include an adjuvant so that cellular immunity will be established effectively. Alternatively, the pharmaceutical compositions or agents of the present invention can be administered with other active ingredients, or can be administered by formulation into granules. An adjuvant refers to any compound, substance or composition that enhances the immune response against the protein when administered together (or successively) with the protein having immunological activity. Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, *salmonella* toxin, IFA (Incomplete Freund's adjuvant), CFA (Complete Freund's adjuvant), ISCOMATRIX, GM-CSF, CpG, O/W emulsion and the like.

Furthermore, liposome formulations, granular formulations in which the peptide is bound to few-micrometers diameter beads, and formulations in which a lipid is bound to the peptide may be conveniently used.

In another embodiment, a peptide of the present invention may also be administered in the form of a pharmaceutically acceptable salt. Examples of preferred salts include, but are not limited to, salts with an alkali metal, salts with a metal, salts with an organic base, salts with an amine, salts with an organic acid (e.g., acetic acid, formic acid, propionic acid, fumaric acid, maleic acid, succinic acid, tartaric acid, citric acid, malic acid, oxalic acid, benzoic acid, methanesulfonic acid and so on) and salts with an inorganic acid (e.g., hydrochloric acid, phosphoric acid, hydrobromic acid, sulfuric acid, nitric acid, and so on). As used herein, the phrase "pharmaceutically acceptable salt" refers to those salts which retain the biological effectiveness and properties of the compound and which are obtained by reaction with inorganic or organic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments, the pharmaceutical compositions or agents of the present invention may further include a component that primes CTLs. Lipids have been identified as components capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As other examples of lipids, *E. coli* lipoproteins, such as tripalmitoyl-S-glycerylcysteinyl-seryl-serine (P3CSS) can be used to prime CTLs when covalently attached to an appropriate peptide (see, e.g., Deres et al., Nature 1989, 342: 561-4).

Examples of suitable methods of administration, include, but are not necessarily limited to, oral, intradermal, subcutaneous, intramuscular, intraosseous, peritoneal and intravenous injection, or such. The administration may be systemic administration or local administration to the vicinity of the targeted sites (i.e., direct injection). The administration can be performed by single administration or boosted by multiple administrations. A pharmaceutically or therapeutically effective amount of the peptide of the present invention can be administered to a subject in need of treatment of cancer or tumor expressing KNTC2. Alternatively, an amount of a peptide of the present invention sufficient to induce CTLs against cancer or tumor expressing KNTC2 can be administered to a subject having cancer expressing KNTC2. The dose of the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 30 mg, for example, 0.1 mg to 10 mg, for example, 0.5 mg to 5 mg, and can be administered once in a few days to a few months, for example, once a week. One skilled in the art can readily determine suitable and optimal dosages.

(2) Pharmaceutical Compositions Containing the Polynucleotides

The pharmaceutical compositions or agents of the present invention can also contain nucleic acids encoding the peptide(s) disclosed herein in an expressible form. Herein, the phrase "in an expressible form" means that the polynucleotide, when introduced into a cell, will be expressed in vivo as a polypeptide that induces anti-tumor immunity. In an illustrative embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922, 687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient's body can be either direct, in which case the patient is directly exposed to a polynucleotide-carrying vector, or indirect, in which case, cells are first transformed with the polynucleotide of interest in vitro, and then the cells are transplanted into the patient. Theses two approaches are known, respectively, as in vivo and ex vivo gene therapies.

For general reviews of the methods of gene therapy, see, Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology that are applicable to the present invention are described by Ausubel et al. in Current Protocols in Molecular Biology (John Wiley & Sons, N Y, 1993); and Krieger in Gene Transfer and Expression, A Laboratory Manual (Stockton Press, N Y, 1990).

Like administration of peptides, administration of polynucleotides may be performed by oral, intradermal, subcutaneous, intravenous, intramuscular, intraosseous, or peritoneal injection, or such. The administration may be systemic administration or local administration (i.e., direct injection) to the vicinity of the targeted sites. The administration can be performed by single administration or boosted by multiple administrations. A pharmaceutically or therapeutically effective amount of the polynucleotide of the present invention can be administered to a subject in need of treatment of cancer or tumor expressing KNTC2. Alternatively, an amount of the polynucleotide of the present invention sufficient to induce CTLs against cancer or tumor expressing KNTC2 can be administered to a subject having cancer expressing KNTC2. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.1 mg to 30 mg, for example, 0.01 mg to 100 mg, for example, 0.1 mg to 10 mg, for example, 0.5 mg to 5 mg, and can be administered once every a few days to once every few months, for example, once a week. One skilled in the art can readily determine suitable and optimal dosages.

X. Methods Using the Peptides, Exosomes, APCs and CTLs

The peptides and polynucleotides of the present invention can be used for preparing or inducing APCs and CTLs. The exosomes and APCs of the present invention can be also used for preparing or inducing CTLs. The peptides, polynucleotides, exosomes and APCs can be used in combination with any other compounds so long as the additional compounds do not inhibit CTL inducibility. Thus, any of the aforementioned pharmaceutical compositions or agents of the present invention can be used for preparing or inducing CTLs. In addition thereto, those including the peptides and polynucleotides can be also used for preparing or inducing APCs as explained below.

(1) Methods of Inducing Antigen-Presenting Cells (APCs)

The present invention provides methods of inducing APCs with CTL inducibility using the peptides or polynucleotides of the present invention.

The methods of the present invention include the step of contacting APCs with the peptides of the present invention in vitro, ex vivo or in vivo. For example, the method of contacting an APC with the peptide ex vivo can include steps of:
a: collecting APCs from a subject, and
b: contacting the APCs of step a with the peptide of the present invention.
The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any one of peptides of the present invention can be used by itself or in combination with one or more of other peptides of the present invention and/or one or more of CTL inducible peptides derived from TAAs other than KNTC2.

On the other hand, when the peptides of the present invention are administered to a subject, APCs are contacted with the peptides in vivo, and consequently, APCs with CTL inducibility are induced in the body of the subject. Thus, the method of the present invention may include the step of administering a peptide of the present invention to a subject to induce APCs with CTL inducibility in the body of the subject. Similarly, when the polynucleotide of the present invention is administered to a subject in an expressible form, the peptide is expressed and contacted with APCs in vivo, and consequently, APCs with CTL inducibility are induced in the body of the subject. Thus, the methods of the present invention may also include the step of administering the polynucleotide of the present invention to a subject to induce APCs with CTL inducibility in the body of the subject. The phrase "expressible form" is described above in section "IX. Pharmaceutical Compositions (2) Pharmaceutical Compositions Containing Polynucleotides".

The method of the present invention may further include the step of introducing a polynucleotide of the present invention into an APC to induce an APC with CTL inducibility. For example, the method can include steps of:
a: collecting APCs from a subject, and
b: introducing a polynucleotide encoding the peptide of the present invention into an APC collected in step a.
Step b can be performed as described above in section "VI. Antigen-Presenting Cells (APCs)".

Alternatively, the methods of the present invention may include the step of preparing an APC that can specifically induce CTL activity against KNTC2, via one of the following steps:
(a) contacting an APC with a peptide of the present invention in vitro, ex vivo or in vivo; and
(b) introducing a polynucleotide encoding a peptide of the present invention into an APC.

Alternatively, the methods of the present invention may include the step of inducing an APC having CTL inducibility, via one of the following steps:
(a) contacting an APC with the peptide of the present invention; and
(b) introducing the polynucleotide encoding the peptide of the present invention into an APC.

The methods of the present invention can be carried out in vitro, ex vivo or in vivo. Preferably, the methods of the present invention can be carried out in vitro or ex vivo. APCs used for induction of APCs having CTL inducibility can be preferably APCs expressing HLA-A2 antigen (i.e., HLA-A2 positive APCs). Such APCs can be prepared by the methods well-known in the arts from peripheral blood mononuclear cells (PBMCs) obtained from a subject whose HLA antigen is HLA-A2. The APCs induced by the method of the present invention can be APCs that present a complex of a peptide of the present invention and an HLA antigen (HLA-A2 antigen) in its surface. When APCs induced by the method of the present invention are administered to a subject in order to induce immune responses against cancer in the subject, the subject is preferably the same one from whom APCs are derived. However, the subject may be a different one from the APC donor so long as the subject has the same HLA type with the APC donor's HLA type.

In another embodiment, the present invention provide agents or compositions for use in inducing an APC having CTL inducibility, and such agents or compositions include one or more peptides or polynucleotides of the present invention.

In another embodiment, the present invention provides the use of a peptide of the present invention or a polynucleotide encoding such a peptide in the manufacture of a composition formulated for inducing APCs.

Alternatively, the present invention further provides the peptide of the present invention or the polypeptide encoding the peptide for use in inducing an APC having CTL inducibility.

(2) Method of Inducing CTLs:

The present invention also provides methods for inducing CTLs using the peptides, polynucleotides, or exosomes or APCs of the present invention.

The present invention also provides methods for inducing CTLs using a polynucleotide encoding both of TCR subunits or polynucleotides encoding each of TCR subunits, wherein the TCR formed by such subunits can recognize (i.e., bind to) a cell-surface complex of a peptide of the present invention and an HLA antigen. Preferably, the methods for inducing CTLs may include at least one step selected from among:

a: contacting a CD8 positive T cell with an antigen-presenting cell that presents on its surface a complex of an HLA antigen and a peptide of the preset invention b: contacting a CD8 positive T cell with an exosome that presents on its surface a complex of an HLA antigen and a peptide of the preset invention; and c: introducing a polynucleotide encoding both of TCR subunits or polynucleotides encoding each of TCR subunits into a CD8 positive T cell, wherein the TCR formed by such subunits can recognize (bind ro) a complex of a peptide of the present invention and an HLA antigen on a cell surface.

When the peptides, polynucleotides, APCs, or exosomes of the present invention are administered to a subject, CTLs are induced in the body of the subject, and the strength of immune responses targeting cancer cells expressing KNTC2 is enhanced. Thus, the methods of the present invention can include the step of administering the peptides, polynucleotides, APCs or exosomes of the present invention to a subject.

Alternatively, CTLs can be also induced by using them ex vivo or in vitro, and after inducing CTLs, the activated CTLs can be returned to the subject. For example, the method can include steps of:

a: collecting APCs from a subject, b: contacting the APCs of step a, with a peptide of the present invention, and c: co-culturing the APCs of step b with CD8 positive T cells.

The APC to be co-cultured with the CD8 positive T cell in above step c can also be prepared by transferring a polynucleotide of the present invention into an APC as described above in section "VI. Antigen-Presenting Cells (APCs)", although the present invention is not limited thereto and thus encompasses any APCs that effectively present on its surface a complex of an HLA antigen and a peptide of the present invention.

One may optionally utilize exosomes that present on the surface a complex of an HLA antigen and a peptide of the present invention instead of the aforementioned APCs. Namely, the present invention can includes the step of co-culturing exosomes presenting on its surface a complex of an HLA antigen and a peptide of the present invention and CD8 positive T cells. Such exosomes can be prepared by the methods described above in section "V. Exosomes". Suitable APCs and exosomes for the method of the present invention present a complex of a peptide of the present invention and HLA-A2 on the surface.

Furthermore, CTLs can be induced by introducing a polynucleotide encoding both of the TCR subunits or polynucleotides encoding each of the TCR subunits into CD8 positive T cell, wherein the TCR formed by such subunits can bind to a complex of a peptide of the present invention and an HLA antigen on a cell surface. Such transduction can be performed as described above in section "VIII. T Cell Receptor (TCR)".

The methods of the present invention can be carried out in vitro, ex vivo or in vivo. Preferably, the methods of the present invention can be carried out in vitro or ex vivo. CD8 positive T cells used for induction of CTLs can be prepared by well-known methods in the art from PBMCs obtained from a subject. In preferred embodiments, the donor for CD8 positive T cells can be a subject whose HLA antigen is HLA-A2. The CTLs induced by the methods of the present invention can recognize cells presenting a complex of a peptide of the present invention and an HLA antigen (e.g., HLA-A2) on its surface. Such CTLs can show specific cytotoxic activity against cells that present a peptide of the present invention on the surface, and therefore, can show specific cytotoxic activity against cells expressing KNTC2 (e.g., cancer cells). When CTLs induced by the method of the present invention are administered to a subject in order to induce immune responses against cancer in the subject, the subject is preferably the same one from whom CD8 positive T cells are derived. However, the subject may be a different one from the CD8 positive T cell donor so long as the subject has the same HLA type with the CD8 positive T cell donor's HLA type.

In addition, the present invention provides a method or process for the manufacture of a pharmaceutical composition for use in induction of a CTL, wherein the method or process includes the step of admixing or formulating a peptide of the present invention with a pharmaceutically acceptable carrier.

In another embodiment, the present invention provides a composition for inducing a CTL, wherein the agent or composition includes one or more peptide(s), one or more polynucleotide(s), one or more APCs, and/or one or more exosomes of the present invention.

In another embodiment, the present invention provides the use of the peptide, polynucleotide, APC or exosome of the present invention in the manufacture of a composition formulated for inducing a CTL.

Alternatively, the present invention further provides the peptide, polynucleotide, APC or exosome of the present invention for use in inducing a CTL.

XI. Methods of Inducing Immune Response

Moreover, the present invention provides methods of inducing immune responses against diseases related to KNTC2. Contemplated diseases include cancer, examples of which include, but are not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor. Preferably, cancer expresses HLA-A2 (i.e., HLA-A2 positive cancer).

The methods of the present invention may include the step of administering an agent or a composition containing any of the peptides of the present invention or polynucleotides encoding them. The inventive methods also contemplate the administration of exosomes or APCs presenting any of the peptides of the present invention. For details, see the item of "IX. Pharmaceutical Compositions", particularly the part describing the use of the pharmaceutical compositions of the present invention as vaccines. In addition, the exosomes and APCs that can be employed for the present methods for inducing immune response are described in detail under the items of "V. Exosomes", "VI. Antigen-Presenting Cells (APCs)", and (1) and (2) of "X. Methods Using the Peptides, Exosomes, APCs and CTLs", supra.

The present invention also provides a method or process for the manufacture of a pharmaceutical composition or agent for use in induction of immune response against cancer, wherein the method or process may include the step of admixing or formulating a peptide of the present invention with a pharmaceutically acceptable carrier.

Alternatively, the method of the present invention may include the step of administrating a vaccine or a pharmaceutical composition or agent of the present invention that contains:

(a) a peptide of the present invention;
(b) a polynucleotide encoding such a peptide of the invention in an expressible form;
(c) an APC presenting a peptide of the present invention on its surface;
(d) an exosome presenting a peptide of the present invention on its surface; or
(e) a CTL of the present invention.

In the context of the present invention, a cancer overexpressing KNTC2 can be treated with these active ingredients. Examples of such cancer include, but are not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor.

Accordingly, prior to the administration of the vaccines or pharmaceutical compositions or agent including any of aforementioned active ingredients, it is preferable to confirm whether the expression level of KNTC2 in cancerous cells or tissues collected from the subject to be treated is elevated as compared with normal cells or tissues collected from the same subject. Thus, in one embodiment, the present invention provides a method for treating cancer (over)expressing KNTC2 in a patient in need thereof, such method including the steps of:

i) determining the expression level of KNTC2 in a biological sample obtained from a subject with the cancer to be treated;
ii) comparing the expression level of KNTC2 with normal control; and
iii) administrating at least one component selected from among (a) to (e) described above to a subject with cancer over-expressing KNTC2 as compared with normal control.

Alternatively, the present invention provides a vaccine or pharmaceutical composition including at least one component selected from among (a) to (e) described above, to be administered to a subject having cancer over-expressing KNTC2. In other words, the present invention further provides a method for identifying a subject to be treated with a peptide of the present invention, such method including the step of determining an expression level of KNTC2 in a subject-derived biological sample, wherein an increase of the expression level as compared to a normal control level of KNTC2 indicates that the subject may have cancer which may be treated with a peptide of the present invention.

Further, in preferred embodiments, the HLA type of a subject may be identified before administering the peptides of the present invention. HLA-A2 positive subjects can be preferably selected for the administration of a vaccine or pharmaceutical composition of the present invention.

Any subject-derived cell or tissue can be used for the determination of the expression level of KNTC2 so long as it can include the transcription or translation product of KNTC2. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from cancerous tissue. Further, if necessary, the cell may be purified from the obtained bodily tissues and fluids, and then used as the subjected-derived sample.

According to the present invention, the expression level of KNTC2 in a biological sample obtained from a subject may be determined. The expression level of KNTC2 can be determined at the transcription (nucleic acid) product level, using methods known in the art. For example, the mRNA of KNTC2 may be quantified using probes by hybridization methods (e.g., Northern hybridization). The detection may be carried out on a chip or an array. The use of an array is preferable for detecting the expression level of KNTC2. Those skilled in the art can prepare such probes utilizing the sequence information of KNTC2. For example, the cDNA of KNTC2 may be used as the probes. If necessary, the probes may be labeled with a suitable label, such as dyes, fluorescent substances and isotopes, and the expression level of KNTC2 may be detected as the intensity of the hybridized labels.

Furthermore, the transcription product of KNTC2 may be quantified using primers by amplification-based detection methods (e.g., RT-PCR). Such primers may be prepared based on the available sequence information of KNTC2.

Specifically, a probe or primer used for the present method hybridizes under stringent, moderately stringent, or low stringent conditions to the mRNA of KNTC2. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing substances, such as formamide.

A probe or primer of the present invention is typically a substantially purified oligonucleotide. The oligonucleotide typically includes a region of nucleotide sequence that hybridizes under stringent conditions to at least about 2000, 1000, 500, 400, 350, 300, 250, 200, 150, 100, 50, or 25, consecutive sense strand nucleotide sequence of a nucleic acid including a KNTC2 sequence, or an anti-sense strand nucleotide sequence of a nucleic acid including a KNTC2 sequence, or of a naturally occurring mutant of these sequences. In particular, for example, in a preferred embodiment, an oligonucleotide having 5-50 in length can be used as a primer for amplifying the genes, to be detected. More preferably, mRNA or cDNA of a KNTC2 gene can be detected with oligonucleotide probe or primer of a specific size, generally 15-30 bases in length. The size may range from at least 10 nucleotides, at least 12 nucleotides, at least 15 nucleotides, at least 20 nucleotides, at least 25 nucleotides, at least 30 nucleotides and the probes and primers may range in size from 5-10 nucleotides, 10-15 nucleotides, 15-20 nucleotides, 20-25 nucleotides and 25-30 nucleotides. In preferred embodiments, length of the oligonucleotide probe or primer can be selected from 15-25 nucleotides. Assay procedures, devices, or reagents for the detection of gene by using such oligonucleotide probe or primer are well known (e.g. oligonucleotide microarray or PCR). In these assays, probes or primers can also include tag or linker sequences. Further, probes or primers can be modified with detectable label or affinity ligand to be captured. Alternatively, in hybridization based detection procedures, a polynucleotide having a few hundreds (e.g., about 100-200) bases to a few kilo (e.g., about 1000-2000) bases in length can also be used for a probe (e.g., northern blotting assay or cDNA microarray analysis).

Alternatively, the translation product of KNTC2 may be detected for the identification of a subject to be treated by the method of the present invention. For example, the quantity of KNTC2 protein (e.g., SEQ ID NO: 79) may be determined. Examples of methods for determining the quantity of the KNTC2 protein as the translation product include, but not limited to, immunoassay methods using an antibody specifically recognizing the KNTC2 protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the KNTC2 protein. Methods to prepare these kinds of antibodies are well known in the art, and any method may be employed to prepare such antibodies and equivalents thereof.

As another method to detect the expression level of KNTC2 based on its translation product, the intensity of staining may be measured via immunohistochemical analysis using an antibody against the KNTC2 protein. Namely, in this measurement, strong staining indicates increased presence/level of the KNTC2 protein and, at the same time, high expression level of KNTC2.

The expression level of the KNTC2 gene in a subject-derived sample can be determined to be increased if the expression level increases from the control level (e.g., the expression level in normal cells) of the KNTC2 by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells by using a sample(s) previously collected and stored from a healthy subject/subjects. In addition, normal cells obtained from non-cancerous regions of an organ that has the cancer to be treated may be used as normal control. Alternatively, the control level may be determined by a statistical method based on the results obtained by analyzing previously determined expression level(s) of KNTC2 in samples from subjects whose disease states are known. Furthermore, the control level can be derived from a database of expression patterns from previously tested cells. Moreover, according to an aspect of the present invention, the expression level of KNTC2 in a biological sample may be compared to multiple control levels, which are determined from multiple reference samples. It is preferred to use a control level determined from a reference sample derived from a tissue type similar to that of the subject-derived biological sample. Moreover, it is preferred to use the standard value of the expression levels of KNTC2 gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level".

Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of KNTC2 is increased as compared to the normal control level, the subject may be identified as a subject with cancer to be treated by administration of a pharmaceutical composition or agent of the present invention.

The present invention also provides a method of selecting a subject for cancer treatment using aforementioned pharmaceutical compositions or agents of the present invention, such method including the steps of:
a) determining the expression level of KNTC2 in biological sample(s) obtained from a subject with cancer;
b) comparing the expression level of KNTC2 determined in step a) with a normal control level; and
c) selecting the subject for cancer treatment by the pharmaceutical compositions or agents of the present invention, if the expression level of KNTC2 is increased as compared to the normal control level.

In some embodiments, such a method may further include the step of identifying a subject having an HLA-A2 (i.e., HLA-A2 positive subject) after or before the steps a) to c) defined above. Methods for HLA typing are well known in the art. For example, PCR-based methods for typing HLA alleles can be used. Antibodies against HLA-A2 are also appropriate tools for identifying HLA types of a subject.

In one embodiment, the present invention further provides a diagnostic kit including one or more peptide of the present invention.

Cancer can be diagnosed by detecting antibodies against one or more peptides of the present invention in a subject-derived sample (e.g., blood, tissue) using a peptide of the present invention.

The subject is suspected to be suffering from cancer, if a subject-derived sample (e.g., blood sample) contains antibodies against a peptide of the present invention and the quantity of the antibodies is determined to be more than the cut off value as compared to control level.

In another embodiment, a diagnostic kit of the present invention may include a peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection of recurrence and/or metastasis of cancer. Further, it can be employed for the selection of subjects applicable with the pharmaceutical compositions that include a peptide of the present invention as an active ingredient, or the assessment of the treatment effect of the pharmaceutical compositions.

Particularly, according to the known method (see, for example, Altman J D et al., Science. 1996, 274(5284): 94-6), the oligomer complex, such as tetramer, of the radiolabeled HLA molecule and a peptide of the present invention can be prepared. With using the complex, the diagnosis can be done, for example, by quantifying the antigen-peptide specific CTLs in the peripheral blood lymphocytes derived from a subject suspected to be suffering from cancer.

The present invention further provides diagnostic agents and methods for evaluating immunological response of subject by using the peptide of the present invention. In one embodiment of the invention, the peptides of the present invention are used as reagents for evaluating or predicting an immune response of a subject. The immune response to be evaluated is induced by contacting an immunogen (i.e., the peptide of the present invention) with immunocompetent cells in vitro or in vivo. In preferred embodiments, the immunocompetent cells for evaluating an immunological response, may be selected from among peripheral blood, peripheral blood lymphocyte (PBL), and peripheral blood mononuclear cell (PBMC). Methods for collecting or isolating such immunocompetent cells are well known in the arts. In some embodiments, any agent that may result in the production of antigen specific CTLs that recognize and bind to the peptide epitope (s) may be employed as the reagent. The peptide reagent need not be used as the immunogen. Assay systems that are used for such an analysis include relatively recent technical developments such as tetramer staining assays, staining for intracellular lymphokines and interferon release assays, or ELISPOT assays. In a preferred embodiment, immunocompetent cells to be contacted with peptide reagent may be antigen presenting cells including dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen-specific cells. The cells can then be identified, for example, by flow cytometry. Such an analysis may be used for diagnostic or prognostic purposes. Cells identified by the procedure can also be used for therapeutic purposes.

The peptides of the present invention may be also used to make antibodies, using techniques well known in the art (see, e.g., CURRENT PROTOCOLS IMMUNOLOGY, Wiley/Greene, NY; and Antibodies A Laboratory Manual, Harlow and Lane, Cold Spring Harbor Laboratory Press, 1989), which may be useful as reagents to diagnose or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein. For instance, the present invention provides a method for diagnosing or detecting a disorder characterized by expression of a KNTC2 polypeptide.

For example, the diagnosis can be done, by a method which allows direct quantification of antigen-specific T cells by staining with Fluorescein-labelled HLA multimeric complexes (for example, Altman, J. D. et al., 1996, Science 274: 94; Altman, J. D. et al., 1993, Proc. Natl. Acad. Sci. USA 90: 10330). Staining for intracellular lymphokines, and interferon-gamma release assays or ELISPOT assays also has been provided. Tetramer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

For instance, in some embodiments, the present invention provides a method for diagnosing or evaluating an immunological response of a subject administered at least one of KNTC2 peptides of the present invention, the method including the steps of:

(a) contacting an immunogen with immunocompetent cells under the condition suitable for induction of CTL specific to the immunogen;

(b) detecting or determining induction level of the CTL induced in step (a); and (c) correlating the immunological response of the subject with the CTL induction level.

In the context of the present invention, the immunogen preferably includes at least one of (a) a KNTC2 peptide having the amino acid sequence of SEQ ID NO: 2, 3, 7, 17, 41, 53 or 68, and peptides having in which such amino acid sequences have been modified with 1, 2 or more amino acid substitution(s). In the meantime, conditions suitable of induction of immunogen specific CTLs are well known in the art. For example, immunocompetent cells may be cultured in vitro under the presence of immunogen(s) to induce immunogen specific CTLs. In order to induce immunogen specific CTLs, any stimulating factors may be added to the cell culture. For example, IL-2 is preferable stimulating factors for the CTL induction.

In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol. Alternatively, the step of evaluation or monitoring of immunological response to the cancer therapy may at the completion of the therapy protocol.

According to the present invention, enhanced induction of immunogen specific CTLs as compared with a control indicates that the subject to be evaluated or diagnosed immunologically responded to the immunogen(s) that has/have been administered. Suitable controls for evaluating the immunological response may include, for example, a CTL induction level when the immunocompetent cells are contacted with no peptide, or control peptide(s) having amino acid sequences other than any KNTC2 peptides. (e.g. random amino acid sequence).

XII. Antibodies

The present invention further provides antibodies that bind to peptides of the present invention. Preferred antibodies specifically bind to peptides of the present invention and will not bind (or will bind weakly) to other peptides. Antibodies against peptides of the invention can find use in cancer diagnostic and prognostic assays. Similarly, such antibodies can find use in the treatment, diagnosis, and/or prognosis of cancers. Moreover, intracellularly expressed antibodies (e.g., single chain antibodies) may therapeutically find use in treating cancers in which the expression of KNTC2 is involved, example of which include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor.

The present invention also provides various immunological assays for the detection and/or quantification of the KNTC2 protein (SEQ ID NO: 79) or fragments thereof, including peptides having amino acid sequences selected from among SEQ ID NOs: 2, 3, 7, 17, 41, 53 and 68. In the context of the present invention, anti-KNTC2 antibodies binding to KNTC2 polypeptide preferably recognize peptide having amino acid sequences selected from among SEQ ID NOs: 2, 3, 7, 17, 41, 53 and 68. The binding specificity of antibody can be confirmed by means of an inhibition test. That is, when the binding between an antibody to be analyzed and full-length of KNTC2 polypeptide is inhibited under presence of any fragment polypeptides having an amino acid sequence selected from among SEQ ID NOs: 2, 3, 7, 17, 41, 53 and 68, such antibody is deemed to specifically bind to the fragment. In the context of the present invention, such immunological assays are performed within various immunological assay formats well known in the art, including but not limited to, various types of radioimmunoassays, immuno-chromatograph technique, enzyme-linked immunosorbent assays (ELISA), enzyme-linked immunofluorescent assays (ELIFA), and the like.

Related immunological but non-antibody assays may also include T cell immunogenicity assays (inhibitory or stimulatory) as well as MHC binding assays. In addition, the present invention contemplates immunological imaging methods capable of detecting cancers expressing KNTC2, example of which include, but are not limited to, radioscintigraphic imaging methods using labeled antibodies of the present invention. Such assays find clinical use in the detection, monitoring, and prognosis of KNTC2 expressing cancers, examples of which include, but are not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor.

An antibody of the invention can be used in any form, for example as a monoclonal or polyclonal antibody, and may further include antiserum obtained by immunizing an animal such as a rabbit with the peptide of the invention, all classes of polyclonal and monoclonal antibodies, human antibodies and humanized antibodies produced by genetic recombination.

An antibody of the present invention can recognize peptides having an amino acid sequence selected from among SEQ ID NOs: 2, 3, 7, 17, 41, 53 and 68. Methods for synthesizing oligopeptide are well known in the arts. After the synthesis, peptides may be optionally purified prior to use as immunogen. In the context of the present invention, the oligopeptide (e.g., 9 or 10 mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, though preferably the compatibility with parental cells used for cell fusion is taken into account. In general, animals of Rodentia, Lagomorpha or Primates may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for the immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies may include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies for use in the context of the present invention, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, wherein a non-human animal is immunized with an antigen for preparing hybridoma, human lymphocytes such as those infected by EB virus may be immunized with a peptide, peptide expressing cells or their lysates in vitro. Then, the immunized lymphocytes may be fused with human-derived myeloma cells that are capable of indefinitely dividing, such as U266, to yield a hybridoma producing a desired human antibody that is able to bind to the peptide can be obtained (Unexamined Published Japanese Patent Application JPS 63-17688).

The obtained hybridomas may then be subsequently transplanted into the abdominal cavity of a mouse and the ascites extracted. The obtained monoclonal antibodies can be purified by, for example, ammonium sulfate precipitation, a protein A or protein G column, DEAE ion exchange chromatography or an affinity column to which a peptide of the present invention is coupled. An antibody of the present invention can be used not only for purification and detection of a peptide of the present invention, but also as a candidate agonists and/or antagonists of a peptide of the present invention.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides for recombinant antibodies prepared as described above.

An antibody of the present invention may be a fragment of an antibody or modified antibody, so long as it binds to the peptide of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F. F. (Pharmacia).

Examples of suitable chromatography techniques, with the exception of affinity chromatography include, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. BIAcore (Pharmacia) may be used to evaluate the activity of the antibody of the present invention.

XIII. Vectors and Host Cells

The present invention also provides for vectors and host cells into which a polynucleotide encoding a peptide of the present invention is introduced. A vector of the present invention finds utility as a carrier of polynucleotides, especially DNA, of the present invention in host cell, to express a peptide of the present invention, or to administer a polynucleotide of the present invention for gene therapy.

When E. coli is selected as the host cell and the vector is amplified and produced in a large amount in E. coli (e.g., JM109, DH5 alpha, HB101 or XL1Blue), the vector should have an "ori" suitable for amplification in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the peptide of the present invention, an expression vector can find use. For example, an expression vector to be expressed in E. coli should have the above characteristics to be amplified in E. coli. When E. coli, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the E. coli is the pelB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from Bacillus subtilis (e.g., pPL608, pKTH50) can be used for producing the peptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Hereinafter, the present invention is described in more detail with reference to the Examples. However, while the following materials, methods and examples may serve to assist one of ordinary skill in making and using certain embodiments of the present invention, there are only intended to illustrate aspects of the present invention and thus in no way to limit the scope of the present invention. As one of ordinary skill in the art will readily recognize, methods and materials similar or equivalent to those described herein can be used in the practice or testing of the present invention.

EXAMPLES

Experimental 1

Materials and Methods

Cell Lines

C1R, HLA-A, B negative mutant lymphoblastoid cell line, and COST, African green monkey kidney cell line, were purchased from ATCC.

Generation of the Stimulator Cells Stably Expressing HLA-A*0201

C1R stable cell line which express HLA-A*0201 (C1R-A02) was used as stimulator cells. To generate stable cell line, electroporation was performed at 1350V, 20 ms pulse and 3 times by Neon transfection system (Invitrogen). The HLA-A*0201 constructs were transfected with the pcDNA3.1 vector (Invitrogen) carrying the neomycin resistance gene. To select stably-transfected cells, G418 (Invitrogen) selection was started on day 2 after transfection. 2 weeks after cultivation, cells were plated on a 96-well plate containing culture medium supplemented with G418. 30 days after plating, HLA-A*0201 expression of proliferating cells was analyzed by FACS (BD Biosciences).

Candidate Selection of Peptides Derived from KNTC2

9-mer and 10-mer peptides derived from KNTC2 that bind to HLA-A*0201 molecule were predicted using "Net-MHC3.2" binding prediction server (www.cbs.dtu.dk/services/NetMHC/) (Buus et al., Tissue Antigens. 2003 November, 62(5):378-84; Nielsen et al., Protein Sci. 2003 May, 12(5):1007-17, Bioinformatics. 2004 Jun. 12; 20(9): 1388-97). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide at 20 mg/ml and stored at −80 degrees C.

In Vitro CTL Induction

Monocyte-derived dendritic cells (DCs) were used as antigen-presenting cells to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells isolated from a normal volunteer (HLA-A*0201 positive) by Ficoll-Paque plus (Pharmacia) solution were separated by adherence to a plastic tissue culture dish (Becton Dickinson) so as to enrich them as the monocyte fraction. The monocyte-enriched population was cultured in the presence of 1000 IU/ml of granulocyte-macrophage colony-stimulating factor (R&D System) and 1000 IU/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro g/ml of each of the synthesized peptides in the presence of 3 micro g/ml of beta 2-microglobulin for 3 hr at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X ray-irradiated (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTL was tested against peptide-pulsed C1R-A02 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 Feb. 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 IU/ml of IL-2 in a total of 150 micro l/well of AIM-V Medium containing 5% AS. 50 micro l/well of IL-2 were added to the medium 10 days later to reach a final concentration of 125 IU/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, IFN-gamma ELISPOT assay and IFN-gamma ELISA were performed. Peptide-pulsed C1R-A02 cells ($1 \times 10^4$/well) were prepared as stimulator cells. Cultured cells in 48-well plate, CTL lines and CTL clones were used as responder cells. IFN-gamma ELISPOT assay and IFN-gamma ELISA were performed under the manufacturer's procedure.

Establishment of the Cells Forcibly Expressing Either or Both of the Target Gene and HLA-A*0201

The cDNA encoding an open reading frame of target genes or HLA-A*0201 was amplified by PCR. The PCR-amplified product was cloned into expression vector. The plasmids were transfected into COS7, which is the target genes and HLA-A*0201-null cell line, using lipofectamine 2000 (Invitrogen) according to the manufacturer's procedure. After 2 days from transfection, the transfected cells were harvested with versene (Invitrogen) and used as the stimulator cells ($5 \times 10^4$ cells/well) for CTL activity assay.

Results

Prediction of HLA-A*0201 Binding Peptides Derived from KNTC2

Table 1a and 1b show the HLA-A02 binding 9 mer and 10 mer peptides of KNTC2 in the order of high binding affinity. A total of 76 peptides having potential HLA-A02 binding ability were selected and examined to determine the epitope peptides.

TABLE 1a

HLA-A*0201 binding 9mer peptides derived from KNTC2

| Start Position | amino acid sequence | Kd (nM) | SEQ ID NO |
|---|---|---|---|
| 330 | GLNEEIARV | 14 | 1 |
| 131 | FLYGFLCPS | 19 | 2 |
| 181 | IVAALVWLI | 21 | 3 |
| 274 | ALNEQIARL | 25 | 4 |
| 549 | GLSEAMNEL | 30 | 5 |
| 327 | KLNGLNEEI | 59 | 6 |
| 184 | ALVWLIDCI | 98 | 7 |
| 588 | MVATHVGSV | 124 | 8 |
| 464 | LLNETEEEI | 126 | 9 |
| 599 | HLEEQIAKV | 127 | 10 |
| 323 | ILDQKLNGL | 162 | 11 |
| 581 | NLQRLLEMV | 182 | 12 |
| 355 | IIDNQKYSV | 289 | 13 |
| 91 | FIQQCIRQL | 325 | 14 |
| 449 | CLVKYRAQV | 356 | 15 |

TABLE 1a-continued

**HLA-A*0201 binding 9mer peptides derived from KNTC2**

| Start Position | amino acid sequence | Kd (nM) | SEQ ID NO |
|---|---|---|---|
| 176 | HTWPHIVAA | 451 | 16 |
| 127 | KIFTFLYGF | 454 | 17 |
| 481 | GLEDTLEQL | 458 | 18 |
| 180 | HIVAALVWL | 478 | 19 |
| 417 | KLARKLKLI | 550 | 20 |
| 218 | GIMHNKLFL | 831 | 21 |
| 163 | ALSKSSMYT | 1032 | 22 |
| 585 | LLEMVATHV | 1060 | 23 |
| 72 | GIFSSSEKI | 1498 | 24 |
| 411 | QLAEYHKLA | 1592 | 25 |
| 129 | FTFLYGFLC | 1659 | 26 |
| 410 | TQLAEYHKL | 1725 | 27 |
| 560 | VQREYQLVV | 1938 | 28 |
| 564 | YQLVVQTTT | 2253 | 29 |
| 492 | MITESKRSV | 3246 | 30 |
| 502 | TLKEEVQKL | 3280 | 31 |
| 534 | SLEKHKHLL | 3460 | 32 |
| 485 | TLEQLNAMI | 3546 | 33 |
| 316 | NLESHSAIL | 4545 | 34 |
| 361 | YSVADIERI | 4545 | 35 |

TABLE 1b

**HLA-A*0201 binding 10mer peptides derived from KNTC2**

| Start Position | amino acid sequence | Kd (nM) | SEQ ID NO |
|---|---|---|---|
| 584 | RLLEMVATHV | 24 | 36 |
| 131 | FLYGFLCPSY | 37 | 37 |
| 313 | YMSNLESHSA | 51 | 38 |
| 393 | KLWNEELKYA | 55 | 39 |
| 163 | ALSKSSMYTV | 56 | 40 |
| 127 | KIFTFLYGFL | 135 | 41 |
| 125 | FLKIFTFLYG | 164 | 42 |
| 354 | NIIDNQKYSV | 245 | 43 |
| 113 | SMKSLQAPSV | 305 | 44 |
| 491 | AMITESKRSV | 410 | 45 |
| 463 | ELLNETEEEI | 532 | 46 |
| 180 | HIVAALVWLI | 564 | 47 |
| 187 | WLIDCIKIHT | 586 | 48 |
| 162 | FALSKSSMYT | 668 | 49 |
| 614 | CMSEDLSENI | 879 | 50 |
| 256 | DLFNVDAFKL | 1047 | 51 |
| 509 | KLDDLYQQKI | 1133 | 52 |
| 322 | AILDQKLNGL | 1184 | 53 |
| 15 | SMQELRSQDV | 1270 | 54 |
| 183 | AALVWLIDCI | 1330 | 55 |
| 541 | LLESTVNQGL | 1339 | 56 |
| 133 | YGFLCPSYEL | 1489 | 57 |
| 223 | KLFLDYTIKC | 1616 | 58 |
| 273 | RALNEQIARL | 1618 | 59 |
| 225 | FLDYTIKCYE | 1778 | 60 |
| 587 | EMVATHVGSV | 1815 | 61 |
| 135 | FLCPSYELPD | 1826 | 62 |
| 228 | YTIKCYESFM | 2153 | 63 |
| 253 | KLKDLFNVDA | 2196 | 64 |
| 129 | FTFLYGFLCP | 2494 | 65 |
| 581 | NLQRLLEMVA | 2681 | 66 |
| 168 | SMYTVGAPHT | 2717 | 67 |
| 185 | LVWLIDCIKI | 2778 | 68 |
| 176 | HTWPHIVAAL | 3257 | 69 |
| 155 | FKDLGYPFAL | 3439 | 70 |
| 259 | NVDAFKLESL | 3792 | 71 |
| 236 | FMSGADSFDE | 4152 | 72 |
| 219 | IMHNKLFLDY | 4307 | 73 |
| 327 | KLNGLNEEIA | 4308 | 74 |
| 298 | KLKASLQGDV | 4873 | 75 |
| 580 | NNLQRLLEMV | 4935 | 76 |

Start position indicates the number of amino acid residue from the N-terminus of KNTC2 dissociation constant [Kd (nM)] is derived from "NetMHC3.2".

CTL Induction with the Predicted Peptides from KNTC2 Restricted with HLA-A*0201

CTLs for those peptides derived from KNTC2 were generated according to the protocols as described in "Materials and Methods". Peptide specific CTL activity was detected by IFN-gamma ELISPOT assay (FIG. 1). The well number #8 with KNTC2-A02-9-131 (SEQ ID NO: 2) (a), #4 with KNTC2-A02-9-181 (SEQ ID NO: 3) (b), #7 with KNTC2-A02-9-184 (SEQ ID NO: 7) (c), #5 with KNTC2-A02-9-127 (SEQ ID NO: 17) (d), #3 with KNTC2-A02-10-127 (SEQ ID NO: 41) (e), #2 with KNTC2-A02-10-322 (SEQ ID NO: 53) (f) and #6 with KNTC2-A02-10-185 (SEQ ID NO: 68) (g) demonstrated potent IFN-gamma production as compared to the control wells. On the other hand, no specific CTL activity was detected by stimulation with other peptides shown in Table 1a and b, despite the fact that such peptides possessed the potential for binding activity with HLA-A*0201. As is typical of negative data, no specific IFN-gamma production was observed from the CTL stimulated with KNTC-A02-9-330 (SEQ ID NO: 1) (h). Taken together, these results suggest that the 7 selected peptides derived from KNTC2 can induce potent CTLs.

Establishment of CTL Line and Clone Against KNTC2 Derived Peptide

Figure 2:
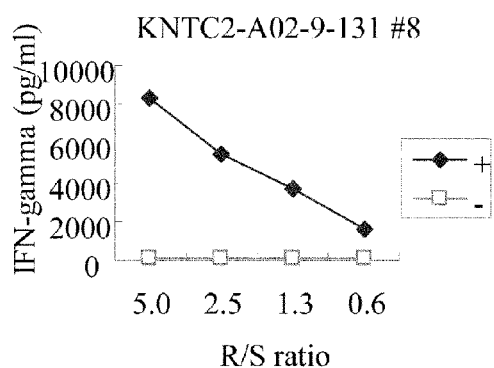
FIG. 2 is composed of a series of line graphs, (a) to (c), depicting the IFN-gamma production of the CTL lines stimulated with KNTC2-A02-9-131 (SEQ ID NO: 2) (a), KNTC2-A02-9-181 (SEQ ID NO: 3) (b) and KNTC2-A02-9-184 (SEQ ID NO: 7) (c). The quantity of IFN-gamma which CTLs produced was measured by IFN-gamma enzyme-linked immunosorbent assay (ELISA). The results demonstrate that CTL lines established by stimulation with each peptide showed potent IFN-gamma production as compared with the control. In the figures, "+" indicates the IFN-gamma production against target cells pulsed with the appropriate peptide, and "−" indicates the IFN-gamma production against target cells not pulsed with any peptides. R/S ratio indicates the ratio of the number of responder cells (CTL line) and stimulator cells.
Figure 2:
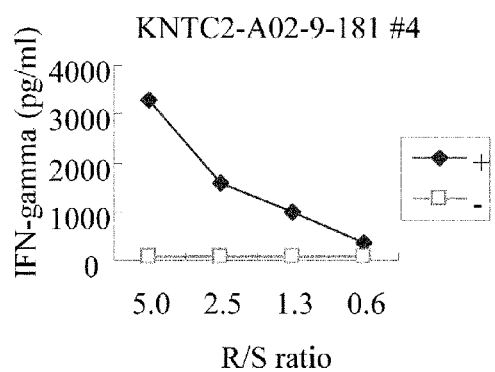
Figure 2:
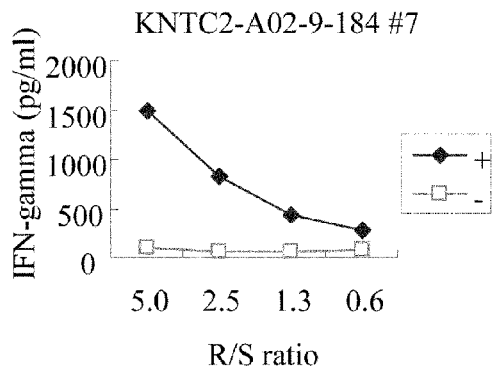
Figure 3:
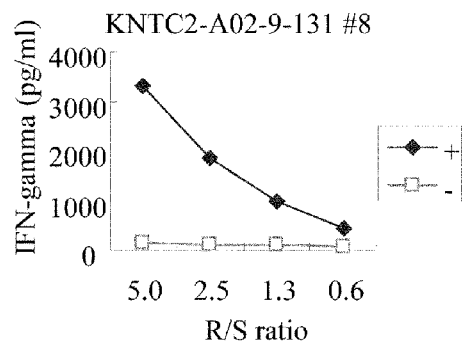
FIG. 3 shows the IFN-gamma production of CTL clones established by limiting dilution from CTL lines stimulated with KNTC2-A02-9-131 (SEQ ID NO: 2) (a), KNTC2-A02-9-181 (SEQ ID NO: 3) (b) and KNTC2-A02-9-184 (SEQ ID NO: 7) (c). The results demonstrate that CTL clones established by stimulation with each peptide showed potent IFN-gamma production compared with the control. In the figure, "+" indicates the IFN-gamma production against target cells pulsed with the appropriate peptide and "−" indicates the IFN-gamma production against target cells not pulsed with any peptides. R/S ratio indicates the ratio of the number of responder cells (CTL clone) and stimulator cells.
Figure 3:
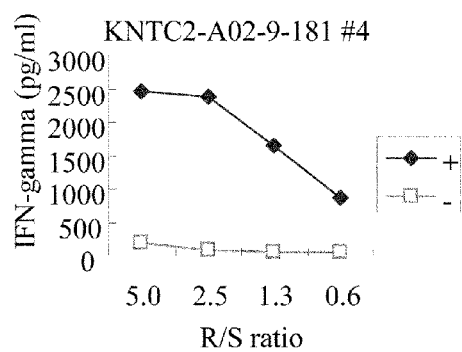
Figure 3:
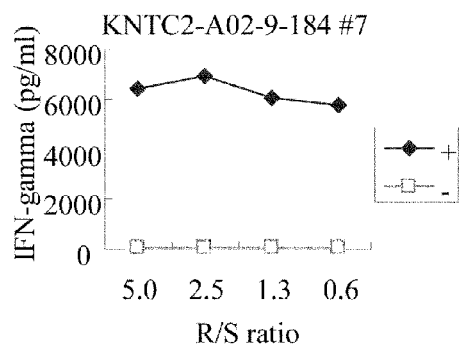

The cells that showed peptide specific CTL activity detected by IFN-gamma ELISPOT assay in the well number #8 with KNTC2-A02-9-131 (SEQ ID NO: 2) (a), #4 with KNTC2-A02-9-181 (SEQ ID NO: 3) (b) and #7 with KNTC2-A02-9-184 (SEQ ID NO: 7) (c) were expanded and the CTL lines were established. CTL activity of these CTL lines was measured by IFN-gamma ELISA (FIG. 2). Those CTL lines demonstrated potent IFN-gamma production against target cells pulsed with the corresponding peptide as compared to target cells without peptide pulse. Furthermore, the CTL clones were established by limiting dilution from the CTL lines as described in "Materials and Methods", and IFN-gamma production from the CTL clones against C1R-A02 cells pulsed with corresponding peptide was measured by IFN-gamma ELISA. Potent IFN-gamma production was observed from the CTL clones stimulated with KNTC2-A02-9-131 (SEQ ID NO: 2) (a), KNTC2-A02-9-181 (SEQ ID NO: 3) (b) and KNTC2-A02-9-184 (SEQ ID NO: 7) (c) (FIG. 3).

Specific CTL Activity Against Target Cells Expressing KNTC2 and HLA-A*0201

Figure 4:
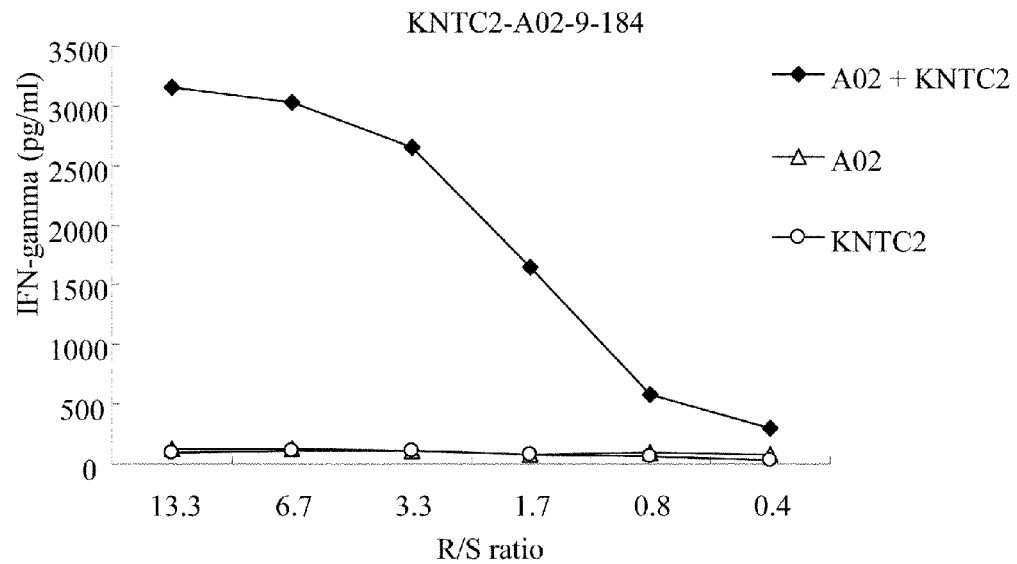
FIG. 4 is a line graph depicting the specific CTL activity of CTL clones against target cells that express KNTC2 and HLA-A*0201. COS7 cells transfected with HLA-A*0201 or the full length KNTC2 gene were prepared as the controls. The CTL line established with KNTC2-A02-9-184 (SEQ ID NO: 7) showed specific CTL activity against COS7 cells transfected with both KNTC2 and HLA-A*0201 (black lozenge). On the other hand, no significant specific CTL activity was detected against target cells expressing either HLA-A*0201 (triangle) or KNTC2 (circle).

The established CTL line raised against KNTC2-A02-9-184 (SEQ ID NO: 7) peptide was examined for the ability to recognize target cells that express KNTC2 and HLA-A*0201 molecule. COS7 cells transfected with both the full length of KNTC2 and HLA-A*0201 gene (a specific model for the target cells that express KNTC2 and HLA-A*0201 gene) were prepared as a stimulator cells, and COS7 cells transfected with either full length of KNTC2 or HLA-A*0201 were used as the controls. In FIG. 4, the CTL line stimulated with KNTC2-A02-9-184 (SEQ ID NO: 7) showed potent CTL activity against COS7 cells expressing both KNTC2 and HLA-A*0201. On the other hand, no significant specific CTL activity was detected against the controls. Thus, this data clearly demonstrates that KNTC2-A02-9-184 (SEQ ID NO: 7) peptide is endogenously processed and expressed on the target cells with HLA-A*0201 molecule and is recognized by the CTLs. These results indicate that this peptide derived from KNTC2 may be available to apply the cancer vaccines for patients with KNTC2 expressing tumors.

Homology Analysis of Antigen Peptides

The CTLs stimulated with KNTC2-A02-9-131 (SEQ ID NO: 2), KNTC2-A02-9-181 (SEQ ID NO: 3), KNTC2-A02-9-184 (SEQ ID NO: 7), KNTC2-A02-9-127 (SEQ ID NO: 17), KNTC2-A02-10-127 (SEQ ID NO: 41), KNTC2-A02-10-322 (SEQ ID NO: 53) and KNTC2-A02-10-185 (SEQ ID NO: 68) are homologous to peptide derived from other molecules that are known to sensitize the human immune system. To exclude this possibility, homology analyses were performed for these peptide sequences using as queries the BLAST algorithm (www. ncbi. nlm. nih. gov/blast/blast. cgi) which revealed no sequence with significant homology. The results of homology analyses indicate that the sequence of KNTC2-A02-9-131 (SEQ ID NO: 2), KNTC2-A02-9-181 (SEQ ID NO: 3), KNTC2-A02-9-184 (SEQ ID NO: 7), KNTC2-A02-9-127 (SEQ ID NO: 17), KNTC2-A02-10-127 (SEQ ID NO: 41), KNTC2-A02-10-322 (SEQ ID NO: 53) and KNTC2-A02-10-185 (SEQ ID NO: 68) are unique and thus, there is little possibility, to our best knowledge, that this molecules raise unintended immunologic response to some unrelated molecule.

In conclusion, the novel HLA-A*0201 epitope peptides derived from KNTC2 identified herein may find utility in the field of cancer immunotherapy.

INDUSTRIAL APPLICABILITY

The present invention provides new epitope peptides derived from KNTC2 that may induce potent and specific anti-tumor immune responses and have applicability to a wide variety of cancer types. Such peptides can find use as peptide vaccines against diseases associated with KNTC2, e.g., cancer, more particularly, bladder cancer, breast cancer, cervical cancer, cholangiocellular carcinoma, chronic myeloid leukemia (CML), colorectal cancer, esophageal cancer, non-small cell lung cancer (NSCLC), lymphoma, osteosarcoma, ovarian cancer, pancreatic cancer, prostate cancer, renal carcinoma, small cell lung cancer (SCLC) and soft tissue tumor.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. An isolated peptide of less than 15 amino acids having cytotoxic T lymphocyte (CTL) inducibility, wherein the peptide comprises
an amino acid sequence SEQ ID NO 7
in which 1 or 2 amino acid(s) are substituted, deleted, inserted and/or added.

2. The peptide of claim 1, wherein the peptide has one or both of the following characteristics:
(a) the second amino acid from the N-terminus of the amino acid sequence of SEQ ID NO: 7 is methionine; and
(b) the C-terminal amino acid of the amino acid sequence of SEQ ID NO: 7 is valine or leucine.

3. The peptide of claim 1, wherein the peptide consists of the amino acid sequence of SEQ ID NO 7 in which 1 or 2 amino acid(s) are substituted, wherein the substitutions are selected from the group consisting of:
(a) the second amino acid from the N-terminus of the amino acid sequence of SEQ ID NO: 7 is methionine; and
(b) the C-terminal amino acid of the amino acid sequence of SEQ ID NO: 7 is valine or leucine.

4. A composition comprising
a peptide of less than 15 amino acids having CTL inducibility, wherein the peptide comprises an amino acid sequence (a) or (b) below:
(a) an amino acid sequence of SEQ ID NO: 7
(b) an amino acid sequence in which 1 or 2 amino acid(s) are substituted, deleted, inserted and/or added in the amino acid sequence of SEQ ID NO: 7
and a pharmaceutical acceptable carrier in combination with an adjuvant.

5. A method for inducing an APC with CTL inducibility, wherein the method comprises the step
of contacting an APC with a peptide of less than 15 amino acids having CTL inducibility, wherein the peptide comprises an amino acid sequence (a) or (b) below:
(a) an amino acid sequence of SEQ ID NO: 7
(b) an amino acid sequence in which 1 or 2 amino acid(s) are substituted, deleted, inserted and/or added in the amino acid sequence of SEQ ID NO: 7.

6. A method for inducing a CTL, wherein the method comprises a step selected from the group consisting of:
(i) co-culturing a CD8 positive T cell with an APC that presents on its surface a complex of an HLA antigen and peptide of less than 15 amino acids; and
(ii) co-culturing a CD8 positive T cell with an exosome that presents on its surface a complex of an HLA antigen and the peptide wherein the peptide has CTL inducibility and comprises an amino acid sequence (a) or (b) below:
(a) an amino acid sequence of SEQ ID NO: 7
(b) an amino acid sequence in which 1 or 2 amino acid(s) are substituted, deleted, inserted and/or added in the amino acid sequence of SEQ ID NO: 7.

7. A method of inducing an immune response against cancer in a subject, wherein the method comprises the step of administering to the subject a composition comprising a peptide of less than 15 amino acids having CTL inducibility, wherein the peptide comprises an amino acid sequence (a) or (b) below:
(a) an amino acid sequence of SEQ ID NO: 7
(b) an amino acid sequence in which 1 or 2 amino acid(s) are substituted, deleted, inserted and/or added in the amino acid sequence of SEQ ID NO: 7.

8. A method of screening for a peptide of less than 15 amino acids having an ability to induce a CTL that has specific cytotoxic activity against a cell that presents a fragment derived from KNTC2, wherein the method comprises the steps of:
(i) providing a candidate sequence consisting of an amino acid sequence modified by substituting, deleting, inserting and/or adding one or two amino acid residue(s) to an original amino acid sequence, wherein the original amino acid sequence is SEQ ID NO 7;
(ii) selecting a candidate sequence that does not have substantial significant homology with the peptides derived from any known human gene products other than KNTC2;
(iii) contacting a peptide consisting of the candidate sequence selected in step (ii) with an antigen presenting cell;
(iv) contacting the antigen presenting cell of step (iii) with a CD8 positive T cell; and
(v) identifying the peptide of which CTL inducibility is same to or higher than a peptide consisting of the original amino acid sequence.

9. The composition of claim 4, wherein the peptide consists of the amino acid sequence of SEQ ID NO: 7.

10. The method of claim 5, wherein the peptide consists of the amino acid sequence of SEQ ID NO: 7.

11. The method of claim 6, wherein the peptide consists of the amino acid sequence of SEQ ID NO: 7.

12. The method of claim 7, wherein the peptide consists of the amino acid sequence of SEQ ID NO: 7.

* * * * *